(12) United States Patent
Cole et al.

(10) Patent No.: US 8,758,433 B2
(45) Date of Patent: Jun. 24, 2014

(54) INSERTION MODE PHACOEMULSIFICATION EMPLOYING POWERED IOL DELIVERY

(75) Inventors: Mark S. Cole, Trabuco Canyon, CA (US); Kevin R. Springer, Santa Ana, CA (US); Rob Raney, Laguna Beach, CA (US); William J. Evans, San Francisco, CA (US); Patrick A. Myall, San Francisco, CA (US); Jonathan Wyler, Boston, MA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 195 days.

(21) Appl. No.: 13/092,462

(22) Filed: Apr. 22, 2011

(65) Prior Publication Data

US 2011/0264102 A1 Oct. 27, 2011

Related U.S. Application Data

(60) Provisional application No. 61/327,435, filed on Apr. 23, 2010.

(51) Int. Cl.
*A61F 2/16* (2006.01)

(52) U.S. Cl.
USPC .......................................... 623/6.12

(58) Field of Classification Search
USPC .......... 606/107, 166; 600/549, 561; 623/6.12, 623/6.11
See application file for complete search history.

(56) References Cited

U.S. PATENT DOCUMENTS

| | | | |
|---|---|---|---|
| 8,308,736 B2 | 11/2012 | Boukhny et al. | |
| 2001/0015593 A1 | 8/2001 | Polla et al. | |
| 2008/0097461 A1 | 4/2008 | Boukhny et al. | |
| 2009/0318933 A1 | 12/2009 | Anderson | |

FOREIGN PATENT DOCUMENTS

EP 2161006 A1 3/2010

*Primary Examiner* — Ryan Severson
(74) *Attorney, Agent, or Firm* — Abbott Medical Optics Inc.

(57) ABSTRACT

A system and method for performing an ocular surgical procedure is provided. The design provides an intra-ocular lens (IOL) to an eye through an incision in the eye by assessing IOL insertion conditions, translating said IOL insertion conditions into a desired force range for insertion of the IOL via the incision, controlling a power source to move the IOL to the eye, monitoring conditions, such as force encountered, while controlling the power source. The design employs feedback of the force encountered and selectively alters force applied based on force encountered.

22 Claims, 21 Drawing Sheets

INSERTION MODE PHACOEMULSIFICATION EMPLOYING POWERED IOL DELIVERY

CROSS-REFERENCES TO RELATED APPLICATIONS

This patent application claims the priority benefit under 35 U.S.C. §119(e) from U.S. provisional patent application 61/327,435 filed on 23 Apr. 2010, the entirety of which is hereby incorporated herein by reference for all purposes as if fully set forth herein.

BACKGROUND OF THE INVENTION

1. Field of the Invention

The present invention relates generally to ocular surgery, and more specifically to an inter-ocular lens (IOL) insertion system, involving generating a powered delivery force for controlling of inter-ocular lens (IOL) insertion during an IOL implantation procedure.

2. Description of the Related Art

Phacoemulsification surgery has been successfully employed in the treatment of certain ocular problems, such as cataracts, and typically entails removing a cataract-damaged lens and implanting of an intraocular lens. Phacoemulsification surgery involves removal of the cataract-damaged lens utilizing a small incision at the edge of the cornea. Through the small incision, the surgeon creates an opening in the capsule, i.e. membrane that encapsulates the lens, and through the opening can remove unwanted lens material and insert a new lens.

During surgery, the surgeon can insert an ultrasonic probe, incorporated within a phacoemulsification handpiece, through the opening in the cornea and capsule, thereby accessing the damaged lens. The handpiece's ultrasonically actuated tip emulsifies the damaged lens for evacuation by the handpiece. After the damaged natural lens is completely removed, the handpiece tip is withdrawn from the eye. The surgeon may now implant an intraocular lens into the space made available in the capsule.

Current techniques for fabricating IOLs employ deformable polymeric materials such as acrylic, silicon, and hydrogel based materials, and the like. For example, Abbott Medical Optics Inc. (AMO) of Santa Ana, Calif., manufactures a brand of aspheric IOL using a single piece of acrylic material called the Tecnis® one piece IOL.

Further, when performing phacoemulsification surgical techniques, such as lens insertion, the deformable polymeric materials enable the surgeon to fold, roll, and manipulate the IOL in a manner sufficient to position and orient the lens for placement within an eye. Once positioned and oriented, the surgeon may manually deliver the configured lens from an insertion cartridge into the eye through a small incision. In general, the insertion cartridge is installed within an IOL insertion system, i.e. a separate delivery handpiece. The surgeon may insert the IOL manually using the IOL delivery handpiece through a delivery tube, in a manner similar to operating a hypodermic needle.

The material properties of flexible acrylic IOLs are highly dependent on the temperature of the surrounding environment, the size of the insertion cartridge, and the ability of a surgeon to provide the precise pressure or force necessary to insert the IOL. In general, the higher the temperature, the softer the IOL material becomes. A warmed IOL may become sufficiently soft, making it easier for the surgeon to fold and manipulate the IOL and deliver the IOL through a small cartridge and through the incision.

However, in general, as the size of the tube of the insertion cartridge is reduced, the delivery force required for implantation increases. A higher delivery force, such as that associated with current small cartridges, may be problematic for the surgeon to control. Any person employing such a device under even near ideal conditions may have difficulty performing IOL implantation using current cartridges in the presence of small ocular incisions.

Currently available manual insertion systems include the aforementioned syringe type and may alternately involve a screw mechanism. Many of these systems are limited in that they require two hands to properly operate. The syringe mechanism requires precision pressure modulation, difficult for almost anyone, while the screw type insertion system is relatively time consuming.

Based on the foregoing, it would be beneficial to offer a single handpiece design for operating an automated IOL insertion system configured for dynamic control of the insertion force, where the surgeon may complete the lens replacement procedure within a sterile field.

Thus there exists a need for a design that facilitates delivery of IOLs that overcomes the foregoing drawbacks present in previously known designs used in the ocular surgical environment.

SUMMARY OF THE INVENTION

According to one aspect of the present design, there is provided a system and method for performing an ocular surgical procedure. The design may comprise a phacoemulsification system designed to provide an intra-ocular lens (IOL) to an eye through an incision in the eye. The design assesses IOL insertion conditions, translates said IOL insertion conditions into a desired force range for insertion of the IOL via the incision, controls a power source to move the IOL to the eye, and monitors conditions, such as force encountered, while controlling the power source. The design employs feedback of the force encountered and selectively alters force applied based on force encountered.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to automated IOL insertion, using a device such as an insertion handpiece, during an ocular procedure and providing a powered delivery force to operate the insertion subsystem. The present design further includes providing heat to the IOL such that the IOL may be provided to the patient at an advantageous temperature. The present arrangement may include a powered delivery force generator configured deliver an IOL into the patient's eye through a small incision, wherein the amount of power delivered is controlled and monitored by a phacoemulsification system. The present design's control and monitoring functionality may comprise a graphical user interface where the surgeon may select, control, and monitor IOL delivery force applied as well as delivery speed, and may account for lens and lens environment temperature, ambient humidity, lens diopter, IOL design, cartridge size, and force limits, such as maximum force limits.

The present arrangement may include a heating generator configured to provide heat for the purpose of warming an IOL, wherein the amount of heat transferred generally provides for a desired lens softness and flexibility. Such heating may occur within an IOL insertion device, or may occur separately from a device or in a maintaining device such as a cartridge either separate from or associated with an insertion device. While generally described herein to heat using a fluid, it is specifically noted that heating may occur without a fluid, either by placing the IOL, cartridge, or delivery device in association with a heat source without fluid present, or heating using electrical, ultrasonic, or other means without fluid present, or using only a minimal quantity of fluid. Heating according to the present design provides a configurable and controlled level of heating in connection with an existing phacoemulsification system.

System Example

While the present design may be used in various environments and applications, it will be discussed herein with a particular emphasis on an environment where a surgeon or health care practitioner performs. For example, one embodiment of the present design is in or with an ocular surgical system that comprises an independent graphical user interface (GUI) host module, an instrument host module, a GUI touchscreen, and a controller module, such as a foot switch, to control the surgical system.

Figure 1:
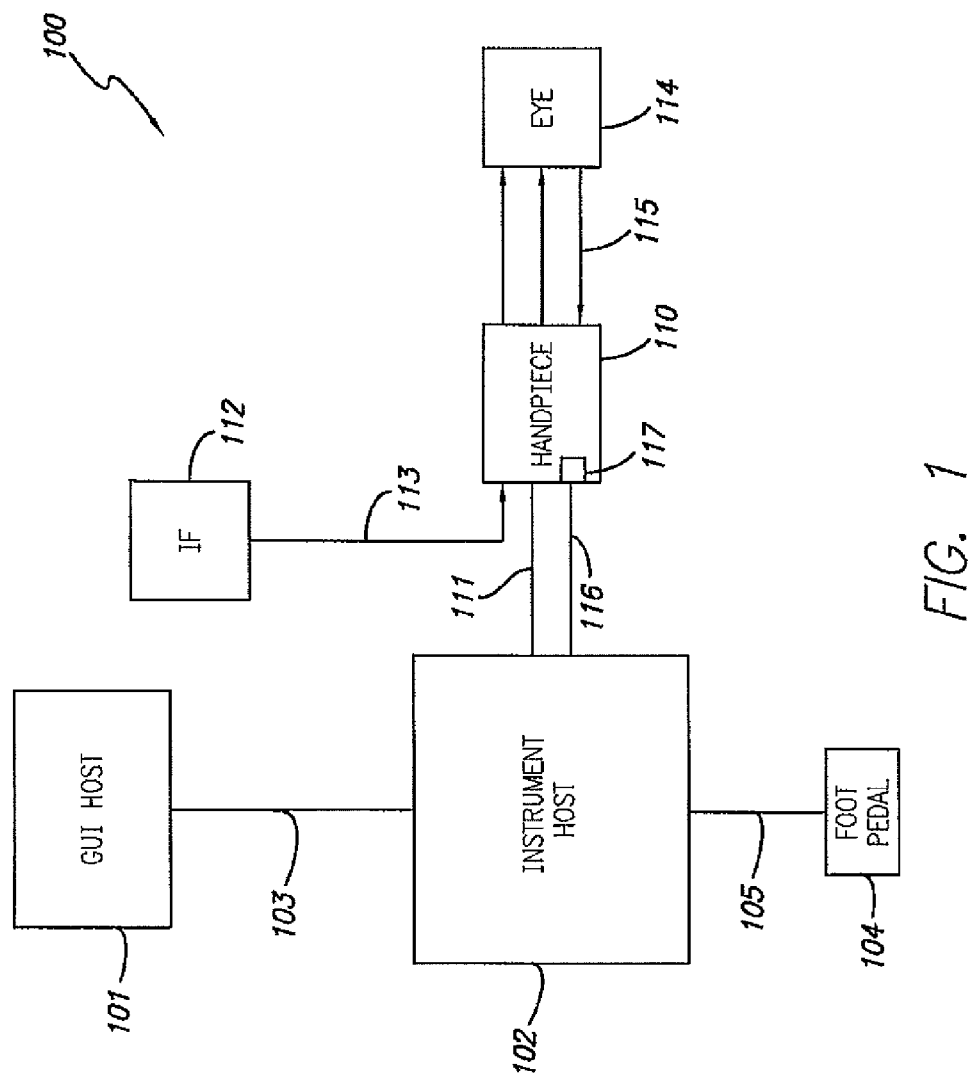
FIG. 1 illustrates an exemplary phacoemulsification/vitrectomy irrigation/aspiration system in a functional block diagram to show the components and interfaces for a medical instrument system that may be employed in accordance with an aspect of the present invention.

FIG. 1 illustrates an exemplary phacoemulsification/vitrectomy (phaco) system 100 in a functional block diagram to show the components and interfaces for a safety critical medical instrument system that may be employed in accordance with an aspect of the present invention. A serial communication cable 103 connects GUI host or GUI host module 101 to instrument host or instrument host module 102 for the purpose of controlling the instrument host 102. Instrument host 102 may be a computer or computing device in this arrangement.

A switch module associated with foot pedal 104 may transmit control signals relating internal physical and virtual footswitch position information to the instrument host 102 over serial communications cable 105. Instrument host 102 may include a database file system for storing configuration parameter values, programs, and other data saved in a storage device (not shown). In addition, the database file system may be realized on the GUI host 101 or any other subsystem (not shown) that could accommodate such a file system.

The phaco system 100 has a handpiece 110 that includes a needle and a device, typically a piezoelectric crystal, configured to ultrasonically vibrate the needle. Instrument host 102 supplies power on line 111 to phacoemulsification and/or vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece. Aspiration is provided to eye 114 by a pump (not shown), such as a peristaltic pump and/or Venturi pump, via instrument host 102, through lines 115 and 116. A surgeon/operator may select an amplitude envelope applied to each pulse via the instrument host and GUI host.

In combination with phaco system 100, the present system enables mechanized control for IOL insertion system functionality in or with the phacoemulsification system and may comprise components including, but not limited to, an ultrasonic handpiece driver, an induced heat source such as a battery, oscillator, diathermy connector, and a chemical reaction, a wet fixture for containment or similar component, and a temperature sensing device or a device having similar functionality.

The mechanized control and monitoring for powered delivery functionality in the present design operates by advancing and retracting an IOL insertion system push rod, alternately or additionally vibrating the push rod, or alternately or additionally rotating the push rod. The present design's new "insertion mode" phaco system operation provides the movements or actions of the push rod operating within the IOL insertion system handpiece and enables control of IOL temperature just prior to use.

Manual IOL Delivery

Figure 2:
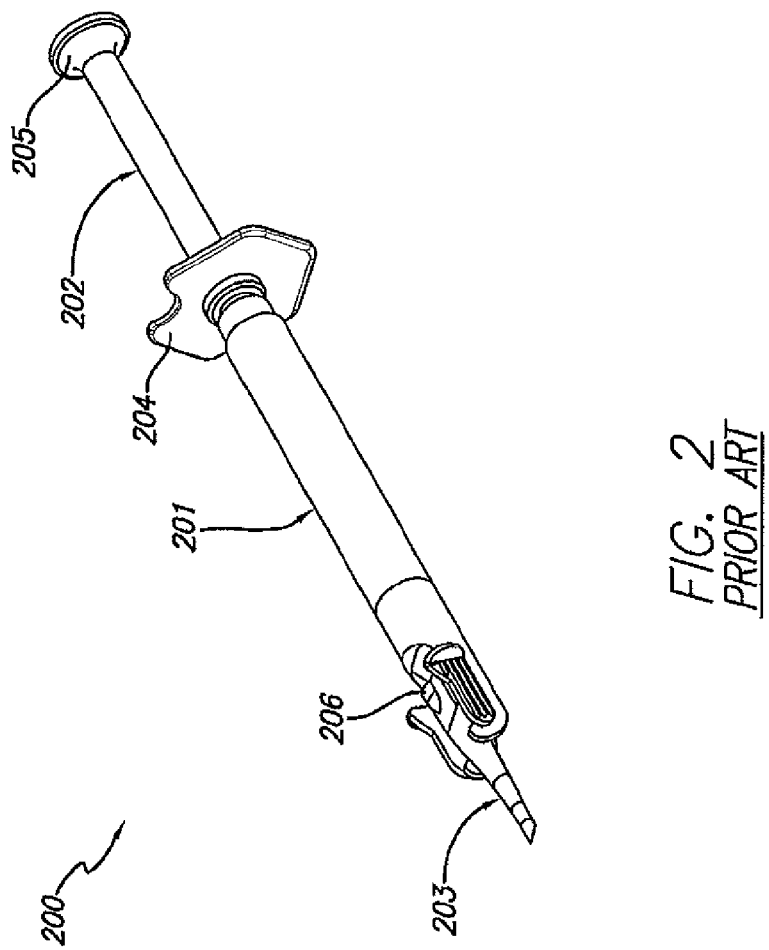
FIG. 2 shows a manual IOL design.
Figure 3:
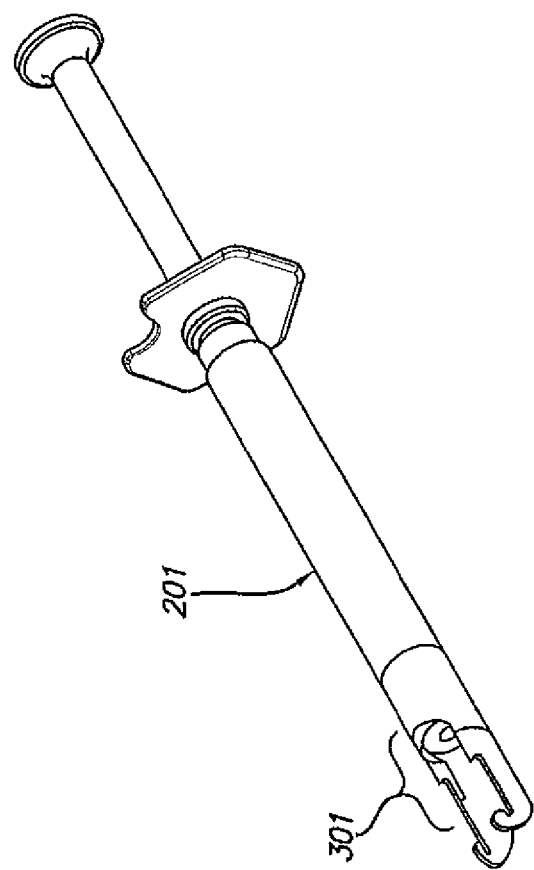
FIG. 3 illustrates a manual standalone handpiece holding station configured to receive an IOL insertion cartridge.
Figure 4:
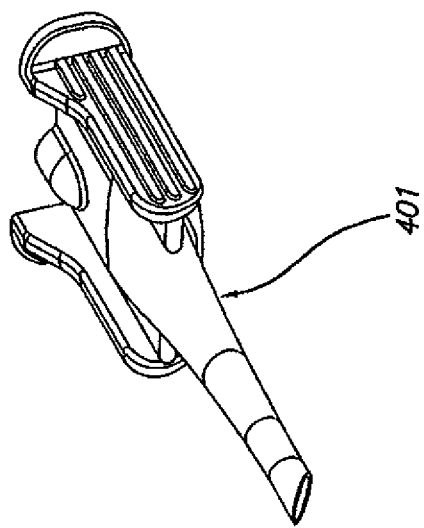
FIG. 4 illustrates an IOL manual insertion cartridge for use with the standalone handpiece holding station.

Previous designs employed to provide IOLs are illustrated in FIGS. 2 through 4. FIG. 2 illustrates an exemplary arrangement for a previously available manually operated IOL insertion system 200. IOL inserter 200 comprises a single handpiece device or handpiece 201 as illustrated in FIG. 2, where handpiece 201 may include plunger 202 and delivery tube 203. The surgeon operates handpiece 201 by grasping the device with a single hand at finger tab 204 and thumb cap 205. Applying force at thumb cap 205 may move plunger 202 along a longitudinal axis defined between plunger 202 and delivery tube 203 at a distal end of cartridge 206, acting as an actuator for purposes moving the lens through delivery tube 203 through an incision into the patient's eye.

The present discussion employs the terms "force" and "pressure" under various circumstances, such as application of force to a rod or application of pressure to the rod. These terms are intended to be accorded their broadest definition and not intended to be limiting, in that the word pressure may be employed to denote force and vice versa.

FIG. 3 illustrates a holding station configured to receive an IOL insertion cartridge. Handpiece 201 comprises holding station 301 configured to receive the IOL insertion cartridge. FIG. 4 illustrates the IOL insertion cartridge for use with a standalone handpiece, such as holding station 301 of FIG. 3. Insertion cartridge 401 comprises a new IOL, configured to be inserted into holding station 301 for use in an ophthalmic surgical procedure.

One example of an IOL manual insertion system similar to that illustrated in FIGS. 2-4 is disclosed in U.S. patent application Ser. No. 12/144,512, "Pre-Loaded IOL Insertion System", inventor Steven R. Anderson, filed Jun. 23, 2008, the entirety of which is expressly incorporated herein.

The present IOL insertion system is configured to automatically generate a powered delivery force as well as controlling the temperature of the IOL prior to delivery.

IOL Insertion System with Powered Delivery

Figure 5A:
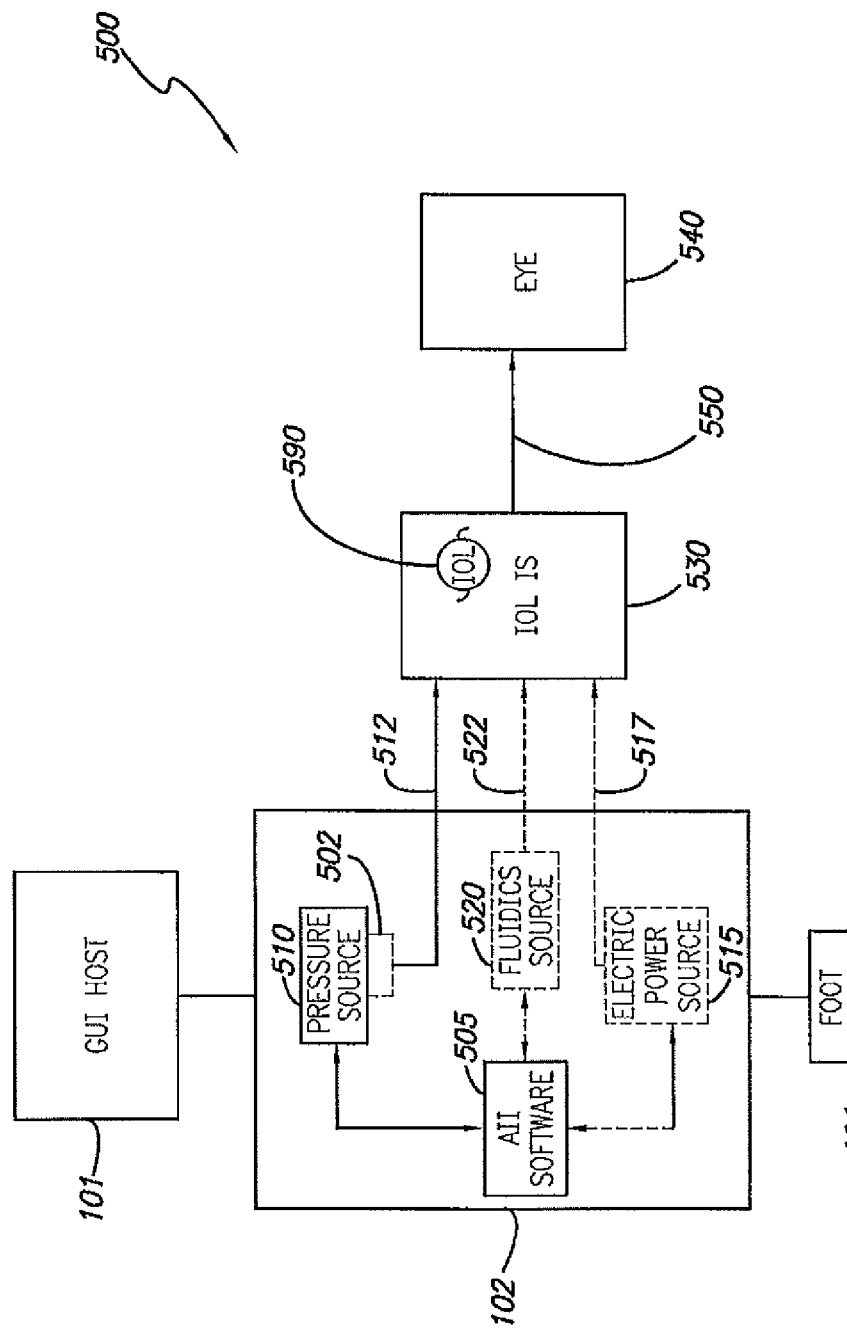
FIG. 5A illustrates a phacoemulsification system configured to control and monitor IOL delivery during a lens replacement surgical procedure in accordance with an aspect of the present design.

The present design provides for automated control of IOL insertion and is generally illustrated in FIG. 5A, where FIG. 5A illustrates phacoemulsification instrument host 102 including software controlling and monitoring facilities arranged for sensing of pressure and application of pressure to an element, such as a rod, configured to push the IOL through the incision and into the ocular cavity. FIG. 5A illustrates one general implementation, and other implementations are possible.

FIG. 5A illustrates the major components, devices, interfaces, and software for an exemplary automated IOL insertion (AII) system 500 in accordance with an aspect of the present design. The present design may employ the AII system to control and monitor IOL delivery during a lens implantation/replacement surgical procedure. AII system software automates control and monitoring for IOL insertion, generating and delivering at least one force to deliver the IOL to an eye, typically through an incision in the eye. The force, or forces, necessary to deliver the IOL are controlled and monitored by the AII system.

The present design may provide a linear force, replacing the need for the surgeon to have to manually push plunger 202, providing a force along a longitudinal axis, moving the IOL through delivery tube 203 as shown in FIG. 2. The AII system may also provide alternate forces, such as a rotational force, or torque, along the longitudinal axis. Such rotational force may move the IOL from a chamber or cartridge separately or in combination with the linear force sufficient to inject the IOL into the patient's eye during an implantation procedure.

Shown in FIG. 5A is pressure source 510 configured to both sense pressure in line 512 and provide pressure via line 512 to IOL insertion system handpiece 530. Pressure source 510 may be any reasonable source of pressure, including but not limited to pneumatic, hydraulic, and electro-mechanical. For example, a pneumatic pressure source may configure a small pneumatic actuator to produce a respiration movement that may move the lens through the injector cartridge, and a hydraulic pressure source may be realized using a small piston within the injector connected to an irrigation or aspiration fluidic supply within the phaco system. The fluidic supply may move the injector piston in a manner sufficient to deliver the lens through the cartridge. An electro-mechanical pressure source may employ a small electric motor to generate vibrations on a push rod.

IOL insertion system handpiece 530 in the implementation of FIG. 5A operates by pressure being applied to a device such as a rod that pushes the IOL through the ocular incision and into the eye 540. The design of FIG. 5A illustrates an IOL insertion system cartridge for use with IOL insertion system handpiece 530, and the handpiece may include a holding station similar to that shown in FIG. 3. An insertion cartridge (not shown in FIG. 5A) comprises a new IOL 590, configured to be inserted into holding station 301 for use in an ophthalmic surgical procedure. Any appropriate type of IOL application delivery mechanism that can operate using pressure to deliver the IOL may be employed.

Pressure source 510 may comprise any appropriate source of pressure depending on the line 512 and handpiece 530 employed, including but not limited to fluid pressure source (gas or liquid) or mechanical pressure source, such as an electronically actuated mechanism. Sensor 502 is shown associated with pressure source 510 and monitors the pressure encountered, whether at the pressure source 510 as shown in the form of backpressure encountered or, for example, by measuring the movement of the rod based on pressure applied, or in some other manner. Sensor 502 may be positioned at any appropriate position in the arrangement shown as long as the pressure encountered may be provided back to instrument host 102 for further processing.

Rather than forcing the IOL into the ocular region at a high rate or only partially, hesitantly, or incompletely delivering the IOL through the incision, the present device provides a relatively even pressure delivery profile for the IOL using a device such as a rod or plunger as the pressure is monitored.

The AAI system employs feedback, sensing the amount of force received and providing a generally reasonable amount of force in response, the response force sufficient to deliver the IOL to eye 540. Instrument host 102 may include hardware, software, or firmware that takes sensed pressure in line 512 and the IOL desired for implantation as well as other selected variables to determine the amount of pressure to be applied to the rod or similar device and provide the IOL through the incision. If a high amount of force is sensed by sensor 502, a higher amount of force can be provided to successfully deliver the IOL to eye 540 or a lower amount of force can be provided to avoid damage to the IOL or control release of the IOL in the eye. Additionally, a drop in pressure sensed in eye 540 or a drop in pressure in or associated with instrument host 102 may result in a drop in pressure applied.

FIG. 5A illustrates a phacoemulsification system configured to control and monitor IOL delivery during a lens replacement surgical procedure. The present design may execute AII software 505 within the computing components available in a phacoemulsification system, for example as illustrated within instrument host 102, or may be realized within GUI host 101, or other suitable software execution environment providing an interface with the phaco system. AII system 500 may provide the necessary data and information for rendering a graphical user interface for the surgeon to configure and operate system functionality.

AII control and monitoring software facilities may therefore include a computer or computing device to adjust and compensate for environmental factors including, but not limited to, environmental conditions such as lens and temperature and ambient humidity, lens diopter (i.e. refractive power), type of IOL design, IOL cartridge size, and parameter limits such as maximum or minimum force applied during delivery. Specifically, AII software facilities may include, but are not limited to, providing a mechanized computational means, realized through execution of one or more software algorithms, to control delivery force and delivery speed for IOL insertion system handpiece 530 based on various selected factors. The present design controls IOL insertion system handpiece 530 to move IOL 590 to eye 540 by injecting or implanting the IOL.

While pressure is shown to be sensed at pressure source 510 in FIG. 5A, pressure may alternately be monitored in the ocular region and force applied based on that pressure sensed. In essence, the present design is seeking to sense the amount of pressure encountered in delivering the IOL to eye 540 and providing a reasonable amount of force on the IOL or rod to deliver the IOL quickly and conveniently to eye 540.

The present design thus provides software control and monitoring of selected components including but not limited to delivery force, IOL delivery speed, lens and lens environment temperature, ambient pressure and humidity, and allows adjustments for diopter, IOL design and dimensions, cartridge size, force limits, and data collected from various sources. The present design enables software in instrument host 102 to adjust the delivery means or delivery mode by advancing/retracting the rod, vibrating and/or rotating the rod to deliver the IOL. Data on selected variables, such as diopter, IOL design, ambient temperature, and so forth, may be maintained in a database or computed based on known equations. For example, if a certain diopter IOL requires an additional 22 mm Hg of pressure as compared with a standard diopter, that amount may be employed in determining the resultant force applied.

Thus as a result, hydraulic or pneumatic pressure may be generated by the phaco system and transferred into linear motion to deliver the IOL. Alternately, electrical energy can be supplied to a motor provided in association with or physically inside IOL insertion system handpiece 530 and controlled by the phaco system.

Control of IOL delivery may be provided using elements shown in FIGS. 1 and 5A. For example, control may be provided by foot pedal 104 or via IOL insertion system handpiece 530. Foot pedal 104 may be employed to control IOL delivery by enabling, via instrument host 102, certain functionality provided using GUI host 101 and software provided therein. A standard single linear or dual linear foot pedal can be employed to actuate or combine various modes of insertion, such as vibration, rotational, etc. insertion modes using the yaw and pitch axes and features of the footpedal. Delivery may be controlled by, for example, the surgeon inducing vibration on the rod using the yaw axis of a dual linear footpedal and inducing rotational motion using the pitch axis of the dual linear footpedal. Various other configurations can be provided enabling the surgeon to control delivery of the IOL. Alternately, a button may be provided, such as on IOL insertion system handpiece 530, that can be used to control IOL delivery in some manner—for example, halting or pausing delivery, or alternately introducing some form of control—torque, vibration, etc.

Figure 5B:
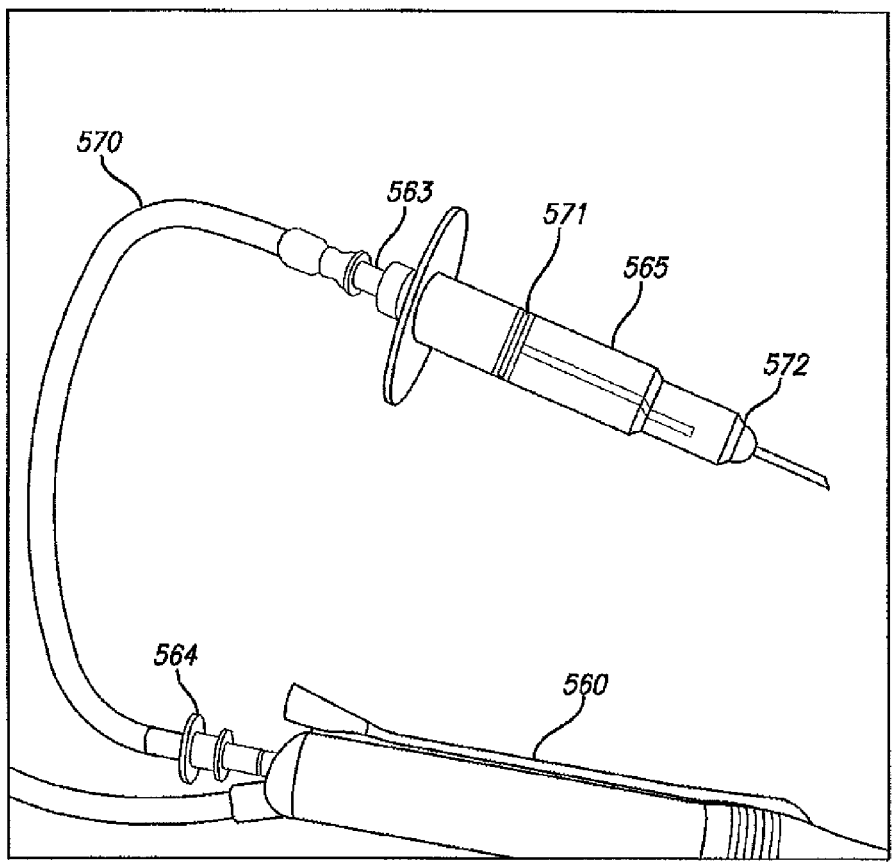
FIG. 5B illustrates an embodiment for powered IOL delivery where a hydraulically driven actuator is controlled by the surgeon operating the foot pedal.

FIG. 5B illustrates a powered IOL delivery device where hydraulically driven actuator 560 is controlled by the surgeon via the foot pedal. Connectors at point 563 and point 564 may provide fluidic communication with the foot pedal controlled phaco system fluidic channels, e.g. irrigation and aspiration, and may operate small piston 571 within IOL insertion system injector handpiece 565. In this arrangement, the phaco system (not shown in this view) may operate handpiece 565 by applying an electrical, mechanical, or electro-mechanical indication to hydraulically driven actuator 560, which applies fluid force via flexible surgical tubing 570. Handpiece 565 may include small piston 571 and other components to deliver the lens located within cartridge 572. The phaco system may operate in a powered reflux mode to deliver the IOL through handpiece 565.

Figure 6A:
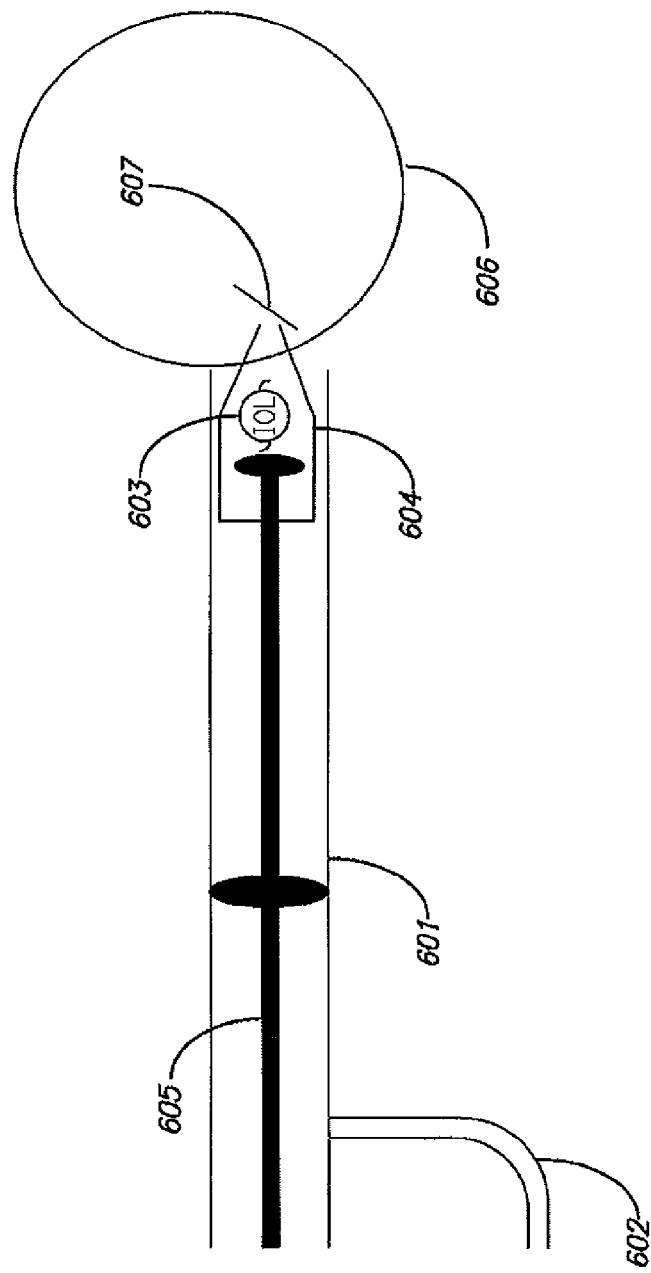
FIG. 6A illustrates an IOL insertion system handpiece configured for powered delivery operation in accordance with the present design.

A generalized view of an example of a delivery device for use in the present design is illustrated in FIG. 6A. The FIG. 6A representation is similar to the IOL insertion system handpiece 530 of FIG. 5A, and includes a body 601, line 602, IOL 603, cartridge 604, and rod 605. From FIG. 6A, rod 605 may be a single rod or may take other forms, including but not limited to a round base or flat round disk having the rod positioned in the center thereof to enable force application over a wide area, or a multiple rod arrangement. Other implementations may be employed. Rod 605 may be moved laterally, torqued, or vibrated to effectuate delivery of IOL 603 from cartridge 604 to eye 606 through incision 607.

The present design may provide for greater control over the insertion process. The system may afford enhanced control in manipulating the IOL and can facilitate insertion using a smaller incision size as compared with current non-powered manual designs. The present design may be employed with insertion systems or injectors that use cartridges, either preloaded or hand loaded with IOLs.

AII system 500 may allow larger delivery forces to be controlled by the surgeon. AII system 500 may allow the surgeon to select, adjust, and control delivery by enabling advancing or retracting rod 605, vibrating rod 605, and/or rotating rod 605, and based on the IOL selected. AII software 505 may be configured to operate pressure source 510 to supply either hydraulic or pneumatic pressure to IOL insertion system handpiece 530 using line 512. In this arrangement, the present design may convert the supplied pressure from pressure source 510 sufficient to transfer into a linear motion for operating rod 605 in IOL insertion system handpiece 530 to deliver IOL 590 into eye 540. Separate from or in concert with pressure source 510, the AII software may be configured to operate an electrical power source 515 and/or a fluidics source 520 to facilitate delivery of IOL 590 to eye 540.

While multiple pressure sources are shown in FIG. 5A, the primary source of pressure is pressure source 510, and the other pressure sources (fluidics source 520 and electric power source 515) may be used in combination with or instead of pressure source 510. A physical device according to the present design may include one, two, or all three of the pressure sources illustrated, and in many cases only one pressure source is employed. Further, while not shown in FIG. 5A, sensors may be provided at appropriate positions with respect to the sources presented. For example, if a configuration employing pressure source 510 and fluidics source 520 is provided, two sensors may be provided to sense pressure for each device, or a single pressure sensor may be provided.

With respect to electrical power source 515, electrical energy may be controlled using a battery, supplied to a motor (not shown) installed within IOL insertion system handpiece 530 using electrical connection 517. AII software 505 controls instrument host 102 electric power source 515 to mechanically move the rod and insert the IOL into eye 540.

Controlling the handpiece motor in this manner, the present design may provide a rotational force impressed on rod 605 to rotate rod 605 about its linear axis. The present design may provide for controlling and monitoring fluidic source 520, such as a reservoir or other fluid source, realized within an existing phaco system instrument host. Fluid force may be provided to IOL insertion system delivery handpiece 530, resulting in linear movement of the rod within the IOL insertion system handpiece when delivering IOL 590. In this arrangement, AII software 505 may control a nozzle or pump or other appropriate fluid pressure mechanism to selectively cause fluid from fluidic source 520 to be delivered to IOL insertion system handpiece 530 via tubing 522.

As described in further detail herein, the present design may provide an interface to control the warming of an IOL. The heated or warmed IOL may have increased material flexibility where the surgeon may elongate, fold, roll, and otherwise manipulate the lens with greater control than previously available designs. Using the present design with automated IOL insertion may allow surgeons to apply greater delivery forces through smaller sized incisions, improving procedure outcomes resulting in shorter healing times and fewer complications.

The surgeon may operate GUI host 101 to select a new phaco system mode, such as 'powered delivery IOL insertion mode', and may select or establish desired operating parameters particular to the delivery conditions, ophthalmic viscosurgical device (OVD) employed, dwell times and relative surgeon skill level. Operating parameters available for input/selection by the surgeon may include but are not limited to, lens temperature and ambient humidity, lens diopter (i.e. refractive power), type of IOL design, IOL cartridge size, and patient case information, such as name, date, and account number. The surgeon may also specify the delivery force type such as linear or rotational direction or vibration level, or a combination thereof, and desired delivery speed.

The AII software algorithms may employ certain preset values. Once the surgeon selects a lens type, the present design may load a previously stored force profile as well as dwell time scenario parameters and/or settings default values. The surgeon may choose to use or modify these values prior to beginning and during conduct of the ocular implant procedure to seek to obtain a smooth delivery of the IOL, or the system may calculate forces based on the values input and information available.

During operational use, the surgeon may want to monitor AII system 500 performance wherein AII software may receive and process signals relating dynamically measured operating values, in near real-time or in real-time, to GUI host 101 for display. The surgeon may view the GUI display to observe and track actual system operating characteristics such as load and pressure feedback. For example, based on measured readings from the processed signals, the surgeon may decide to either start or stop the handpiece electric motor to increase or decrease the amount of torque or linear force applied to the rod. In another example, the surgeon may operate the pressure source to ratchet the rod forward, in precise increments, to ultimately move the IOL into the eye.

In the situation where the surgeon has selected a precise fluidic control pressure delivery range, such as 100-200 mmHg, and the observed or measured pressure exceeds 200 mmHg, an algorithm executing as part of AII software 505 may stop or reduce operation of fluidics source 520 until the pressure is reduced until it returns to the desired range. The surgeon may manually control the pressure delivered to the IOL Insertion system needle. For example, to decrease pressure, the system may remove or reduce the supply of pressure to the IOL insertion system handpiece, for example by the surgeon releasing foot pedal 104, affording control over the amount of force delivered to the rod or handpiece.

In the situation where the surgeon has selected to use a rotational force, or to add the rotational force to a linear force supplied from fluidic source 520, and the torque delivered exceeds establish parameter settings, an algorithm executing as part of AII software 505 may stop or reduce the electrical energy supplied from power source 515 to the motor in the handpiece until the desired torque range is realized. The software is configured such that the surgeon may personalize the behavior of the system software by entering custom phaco system settings for use by the phaco 'insert mode' software application. AII system monitoring capabilities may also involve measuring vacuum levels present within the patient's eye capsule and may include a feedback algorithm for comparing measured vacuum with desired vacuum. The feedback algorithm may provide additional data and information for the AII system to process for the control of delivery process.

The present design may provide for an automated comparison between the surgeons desired/selected parameters and actual measured results from various sensors, such as pressure, vacuum, temperature, voltage, etc., and may store the surgeons selected parameter values or settings. The AII system software may provide monitor and control facilities and may be configured to determine whether measured values reported by the sensors are within or out of the desired settings.

If a parameter has fallen below its specified range, AII software 505 may instruct instrument host 102 to report via the GUI host a visual indication such as a text message or flashing ICON, or provide an audible alarm to notify the surgeon and may indicate the currently observed parameter values rendered by the GUI display. For example, if the pressure is too low, or too high, the system may indicate that the software is automatically adjusting the parameter to its desired operating range, or warn the surgeon to perform a manual adjustment. If the measured pressure rises to or above the selected range, AII software 505 may instruct instrument host 102 to report a "range exceeded" indication via GUI host 101, such as using visual and/or audible indications and combinations thereof.

AII system 500 may also provide for use of a foot pedal, such as a single linear or dual linear design, by a surgeon to control the IOL during delivery. In the situation where a dual linear foot pedal is available for use, the surgeon may operate foot pedal 104 to combine different modes of insertion, including but not limited to, vibration, rotation, linear, IOL orientation, etc., realized through the pitch and yaw capabilities available within foot pedal 104 or may use a switch disposed on the IOL delivery handpiece to control delivery.

In short, the present design may provide a small electric motor within the IOL insertion system handpiece where an electrical connector is provided for plugging into the foot pedal controlled phaco system. By operating the foot pedal, the surgeon may control the electric motor for powered IOL delivery.

Figure 6B:
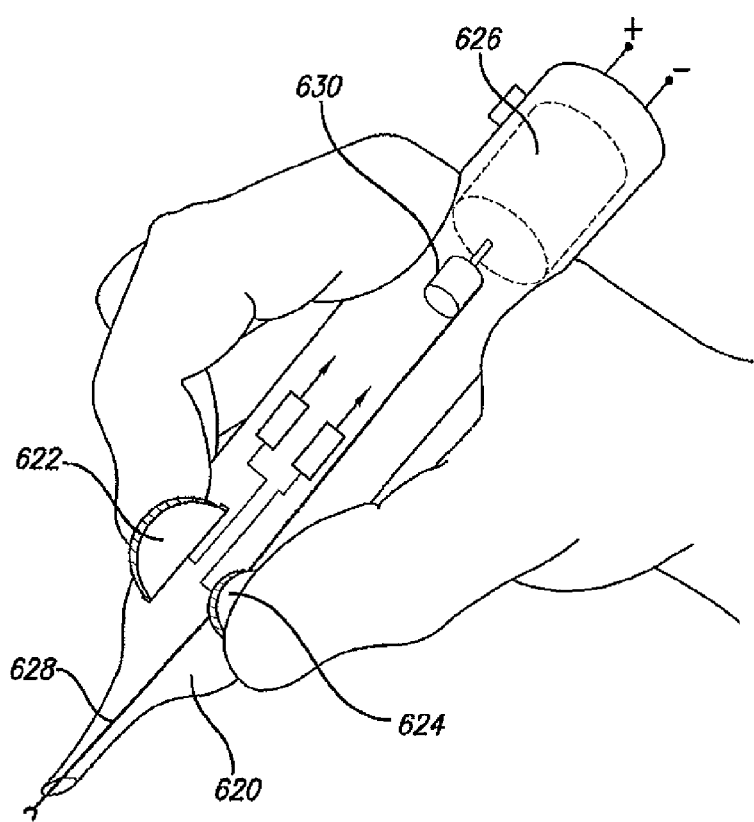
FIG. 6B illustrates an embodiment for powered IOL delivery where an electric motor is controlled through finger input at the handpiece from the surgeon.

FIG. 6B illustrates an embodiment for powered IOL delivery where controlling an electric motor is realized through finger inputs at the handpiece from the surgeon. In this arrangement, the surgeon may operate the powered IOL delivery system fingertip controls located on handpiece 620. The present design may employ velocity control dial 622 and forward/reverse direction switch 624 to control motor 626 within handpiece 620. Motor 626 may operate pushrod 628 by rotating gearbox 630, where the gearbox may involve a worm drive such as a rack and pinion or a ball screw drive arrangement to transfer vibrations and other forces generated by electric motor 626 to pushrod 628.

Figure 7:
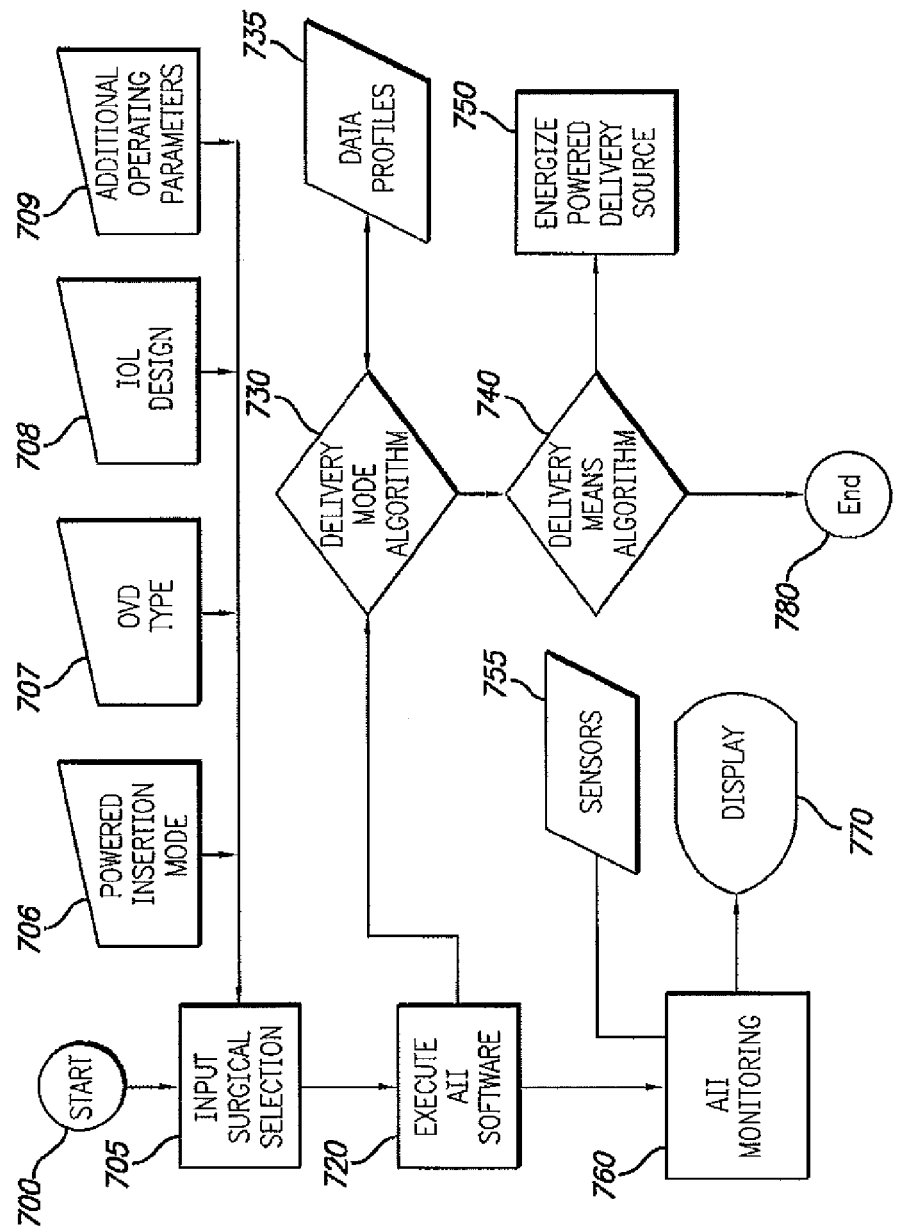
FIG. 7 is a flowchart illustrating general operation of the AII (Automated IOL Insertion) system software to control powered delivery for inserting the IOL.

FIG. 7 is a flowchart illustrating general operation of system software to control powered delivery for inserting an IOL in accordance with an aspect of the present design. The surgeon may operate the AII software to control and monitor the powered delivery for an IOL, IOL cartridge, or IOL insertion system by operating the instrument host to start the AII software. The surgeon may input surgical selections 705 to establish desired operating parameters and settings, including for example powered insertion mode 706, OVD type 707, IOL design 708, and additional operating parameters 709, including but not limited to type of IOL design, IOL cartridge size, and force limits.

Based on the inputs received, executing AII software 720 may determine the delivery mode and forces needed to effectuate delivery. Delivery mode algorithm 730 may access data profiles 735 to obtain data relating the desired operation, and may determine at least one delivery mode such as advance rod, retract rod, rotate rod, vibrate rod, and any combinations thereof for controlling the powered delivery mode. Feedback pressure may also be employed to determine the desired delivery mode and force.

Delivery means algorithm 740 may determine at least one delivery mechanism, where appropriate, such as hydraulic, pneumatic, electrical, and fluidic drive, and any combinations thereof to control powered IOL delivery. In one arrangement, AII software algorithms and processes may involve the use of preset values. For example, once the surgeon selects IOL design 708, the present design may load previously stored data profile 735 and other parameters and settings default values stored locally. The surgeon may choose to use or modify these values using surgical selection module 705, before and during the ocular implant procedure.

AII monitoring 760 may allow the surgeon to monitor desired parameters, including but not limited to receiving and processing measured operating values received from sensors 755. Desired parameters or performance may be provided using display 770. The surgeon may observe and track operational conditions of the IOL and powered delivery system during the ocular surgical procedure. Upon successful implantation, the AII software may stop or end execution at point 780.

AII monitoring capabilities may also involve measuring various operational conditions, such as vacuum levels present within the patient's eye capsule, and may include a feedback algorithm, not shown in FIG. 7, for comparing measured operational conditions with desired operational conditions. The feedback algorithm may provide additional data and information for the AII system to process for the control of delivery process.

In sum, the present design may provide for control and monitoring of an automated IOL insertion system, and may dynamically adjust to vary the operation of the linear and rotational force generating sources, e.g. fluidics, pressure, and electrical, in response to changes in surgical and environmental conditions. The present design may involve a wide range of force generation and transfer methods for pushing and twisting the IOL insertion system plunger to move and implant the IOL while maintaining within a sterile field. For example, the force generating source may be cycled on and off over time to incrementally advance or retract the rod, where the cycle duty rate may be controlled by pre-established profiles, and/or user established settings. The present design may provide for automated IOL insertion affording control over high delivery forces providing mechanized linear and rotational forces to move the rod within an IOL delivery handpiece during lens implantation surgical procedures.

Movement of the rod may take varying forms. In addition to the movements described above, the rod may advance and retract, or may retract under specific conditions. Turning or rotating of the rod may be provided, and the IOLs may be pushed or pulled depending on desired performance under the conditions encountered. Control may be provided via the surgeon or via the computer software discussed herein. For example, the system may retract or pull the rod in instances where an excessive amount of force is necessary to deliver the IOL, and a problem condition may be indicated.

IOL Insertion System with Heated Delivery

The present design may warm the IOL, IOL cartridge, or IOL insertion system, where operating room personnel provide heat to a liquid solution, contained in a wet fixture, using the phacoemulsification/vitrectomy handpiece needle. With the needle present in the solution, the surgeon may control heat transferred by ultrasonic needle vibrations, where the solution conducts heat to the IOL.

Figure 8:
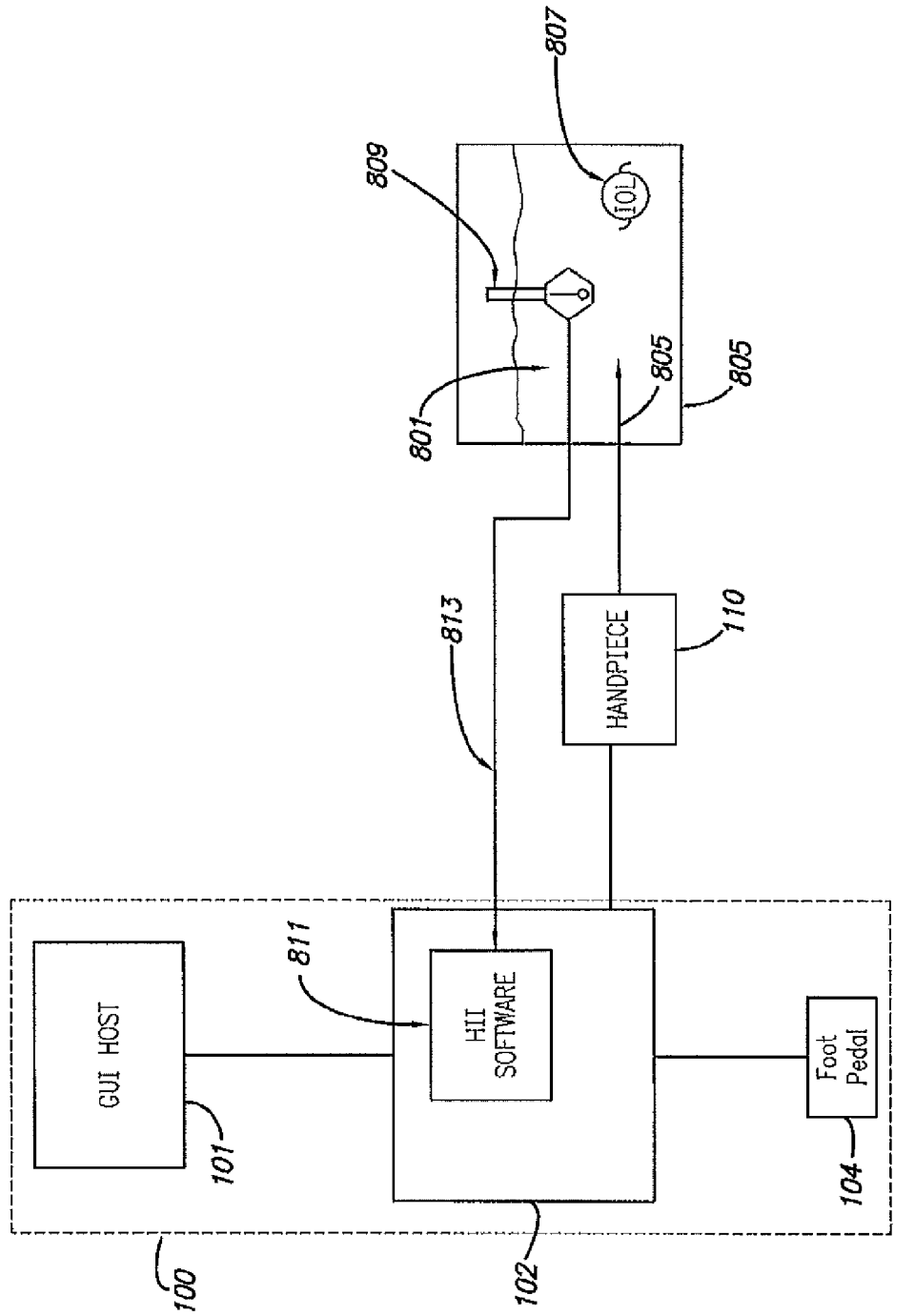
FIG. 8 illustrates a heating source mechanism arranged to transfer heat into an IOL from the phacoemulsification handpiece in accordance with the present design.

FIG. 8 illustrates an existing phaco system configured to provide heat to an IOL, IOL cartridge, or IOL Insertion System, using the phacoemulsification/vitrectomy handpiece. Phaco system 100 may include software controlling and monitoring functionality for transferring heat to an IOL prior to folding, rolling, and/or manipulating the IOL. Such heating prepares the IOL prior to delivery. In this arrangement, the surgeon may place IOL 807 into wet fixture 803 containing liquid solution 801. After inserting ultrasonic needle 805 into liquid solution 801 containing IOL 807, the surgeon may operate phacoemulsification or vitrectomy handpiece 110 where the needle vibrations may transfer heat into the solution.

With the needle present in the solution, the heat transferred into the solution may warm the lens through heat conduction or heat transfer. The surgeon may control the heat transfer from the needle vibrations to the IOL by applying power to the ultrasonic handpiece, for example by pressing and controlling foot pedal 104. Vibrating liquid solution 801, e.g.

water, balanced salt solution (BSS), or other suitable fluid, in wet fixture 803 may be warmed from agitating the molecules in the solution using ultrasonic energy.

Although FIG. 8 illustrates the present design for warming IOL 807, the present design may be configured to warm liquid solution 801 where an IOL cartridge or IOL insertion system is placed in liquid solution 801 where IOL 807 is contained therein (not shown). The present design's wet fixture 803 arrangement may provide for transferring heat from the vibrating needle into the IOL, IOL cartridge, or IOL insertion system prior to insertion while maintaining a sterile field.

The present design may employ temperature sensor device 809 configured to measure and report the temperature of wet fixture 803 liquid solution 801, and thus the IOL 807 itself, to instrument host 102. In this arrangement, temperature sensor 809 may communicate measured temperature values to heated IOL insertion (HII) software 811 across communication connection path 813, forming a control feedback loop. The surgeon may input his desired or personalized settings and parameter values used in operating the HII software via selection menus rendered by phaco system GUI host 101.

Figure 9A:
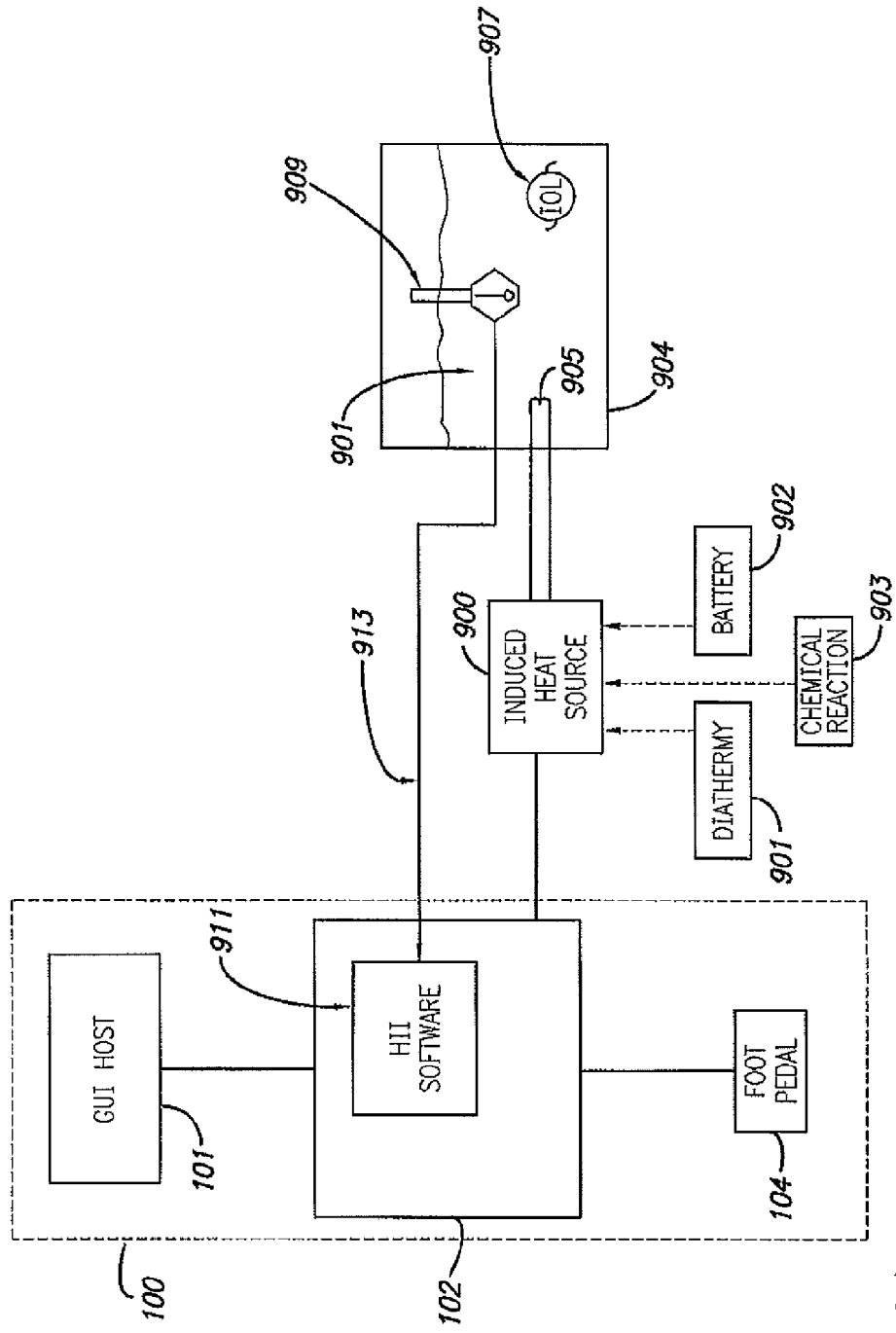
FIG. 9A illustrates a heating source mechanism arranged to transfer heat into an IOL from an induced heat source that may be employed in accordance with the present design.

In another embodiment, the instrument host may control heat transfer from an induced or inductive heat source to the IOL. Induced or inductive heat may be generated in various ways, wherein heat is transferred from the heat source to the liquid solution held in the wet fixture. Induced or inductive heat sources may include, but are not limited to, an electric diathermy connector using high frequency alternating electric or magnetic fields, or a unit such as an ultrasonic power oscillator with a resonant circuit, an electrical battery, or a chemical reaction, as illustrated in FIG. 9A. In addition, the present design may involve a dielectric heating element (not shown in FIG. 9A) where ultrasound or electromagnetic radiation, such as radio wave or microwave frequency, is configured to heat a dielectric material positioned in wet fixture 904.

FIGS. 9A through 15 illustrate the major components, devices, interfaces, and software for an exemplary automated IOL heat generation and transfer system that may be employed in accordance with the present design. FIG. 9A illustrates use of an induced heat source that may be employed in accordance with an aspect of the present design. The present design may operate the induced heat conduction mechanism and control heat transfer into an IOL. Software in the instrument host 102 may provide for temperature sensing and a temperature feedback control loop.

In the arrangement illustrated in FIG. 9A, operating room personnel may place an IOL into wet fixture 904 containing liquid solution 901. After inserting IOL 907 into liquid solution 901, the surgeon may operate the instrument host by inputting settings and selections relating desired control for transfer of heat from induced heat source 900 into the wet fixture containing liquid solution 901, e.g. water or balanced salt solution (BSS), and suspended IOL 907. Instrument host 102 may execute HII software 911 and provide instructions for operating induced heat source 900 while monitoring the measured temperature of liquid solution 901 reported from temperature sensor 909. HII software 911 may provide operational control for a diathermy 901 connector heating device, battery 902 device, or chemical reaction 903 device, or other devices acting as heat sources. Induced heat source 900 may be a thermal conduction 905 device or other device capable of transferring heat from induced heat source 900 into liquid solution 901.

Although FIG. 9A illustrates warming IOL 907, the present design may warm liquid solution 901, where an IOL cartridge or IOL insertion system is placed in the liquid containing IOL 907. Such an arrangement is not shown in FIG. 9A. The wet fixture arrangement may provide the surgeon a way of transferring heat from the induced heat source into the IOL, IOL cartridge, or IOL insertion system while maintaining a sterile field.

The present design may comprise a temperature sensor 909 configured to report the temperature of the wet fixture liquid solution 901 to instrument host 102. In this arrangement, temperature sensor 909 may communicate measured temperature values to HII software 911 across communication connection path 913.

Figure 9B:
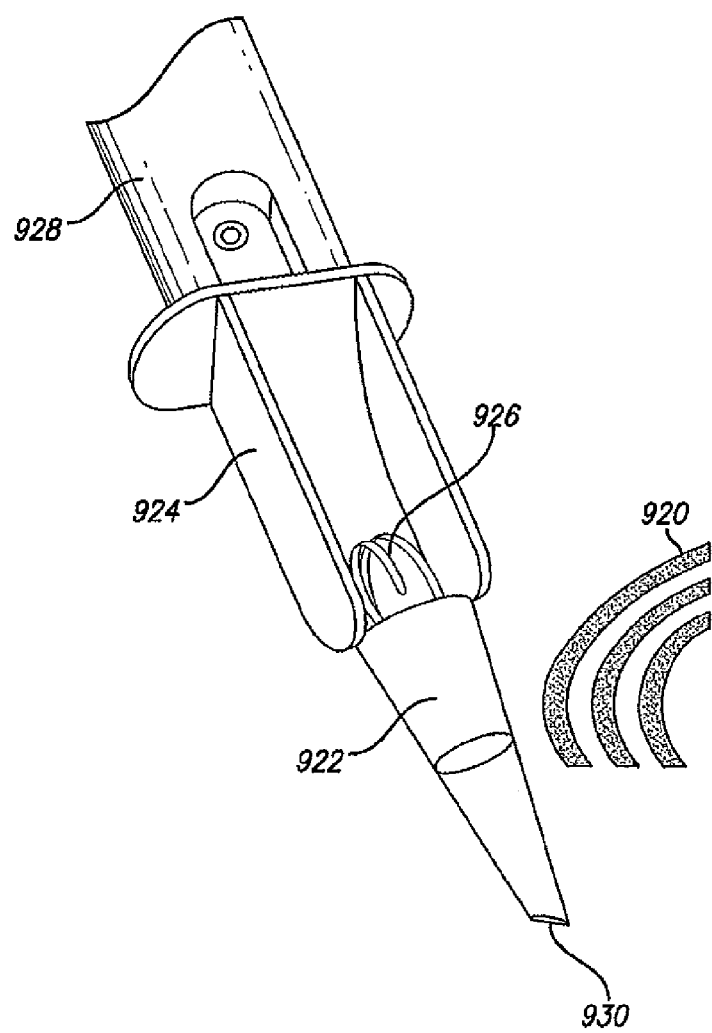
FIG. 9B illustrates an embodiment of a phacoemulsification insertion system injection device employing an induction heater within the sterile field.

FIG. 9B illustrates an embodiment for IOL insertion system, or injector, where an induction heater may be located within the sterile field. In this arrangement, the present design may involve use of high powered magnetic field 920 to excite metal band 922 attached to the outside of cartridge 924 holding loaded IOL 926. This excitation may produce heat for transfer into the IOL. When the IOL cartridge is sufficiently heated to the desired insertion temperature, the surgeon may operate handpiece 928 to move heated IOL 926 through distal tip 930 and deliver the warmed IOL from the cartridge to the patient's eye.

Figure 10:
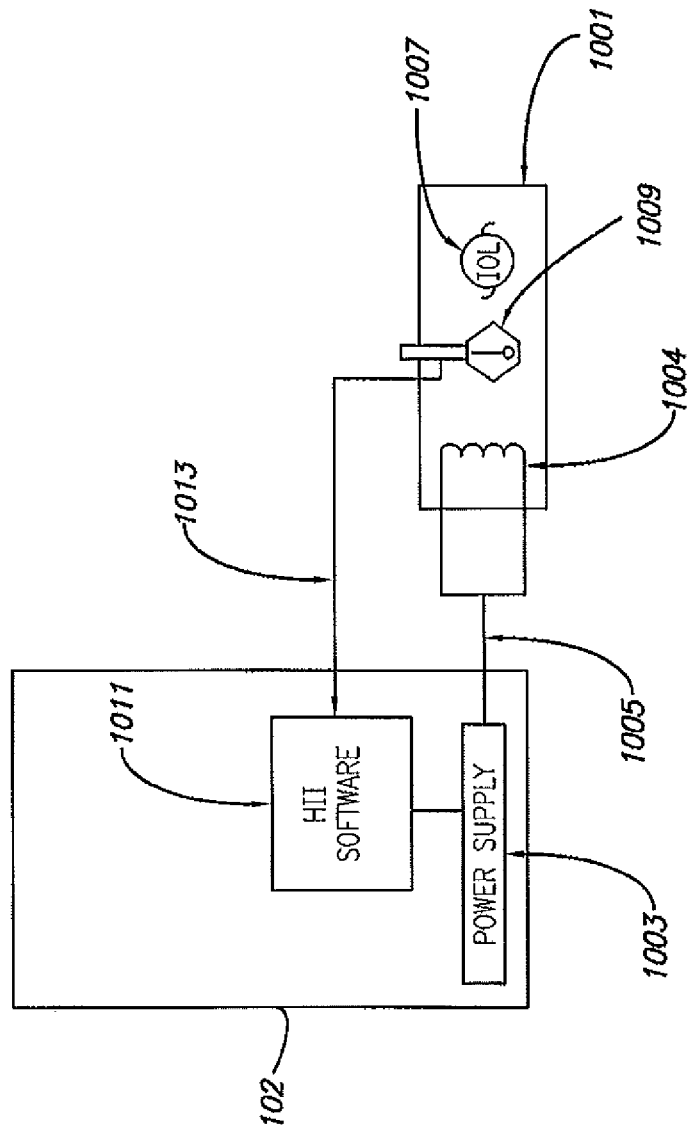
FIG. 10 illustrates a heating element mechanism integrated within a dedicated IOL Insertion System that may be employed in accordance with the present design.

In another embodiment, the present design may warm a dedicated IOL insertion system. Instrument host 102 may provide a heating element integrated within the dedicated IOL Insertion System. FIG. 10 illustrates the phacoemulsification instrument host configured to provide power to a heating element mechanism integrated within the dedicated IOL Insertion System. The integrated heating element 1004 may induce heat using power supply 1002 into dedicated IOL insertion system 1001 and warm IOL 1007.

The present design may configure a component within phaco system 100 to provide software control and monitoring facilities for integrated heating element 1004. Heat may be transferred from the heating element into IOL 1007 prior to folding, rolling, and manipulating, allowing the surgeon to configure the lens prior to implantation.

In the arrangement of FIG. 10, operating room personnel may cause power supply 1003 to be connected to integrated heating element 1004 using cable 1005. The surgeon may operate the instrument host by inputting desired heat control settings for transfer of heat from integrated heating element 1004 into IOL 1007. Instrument host 102 may execute HII software 1011 and provide instructions to operate power supply 1003 while monitoring the measured temperature of dedicated IOL insertion system 1001 using integrated temperature sensor 1009. Temperature is monitored and controlled using simple feedback, seeking to establish and maintain a desired temperature where the present design feedback signals may be communicated to HII software 1011 across communication connection path 1013. In short, the present design may arrange a small electric heater integrated with the IOL insertion system, i.e. injector, for providing heat transfer into an IOL loaded cartridge.

Figure 11A:
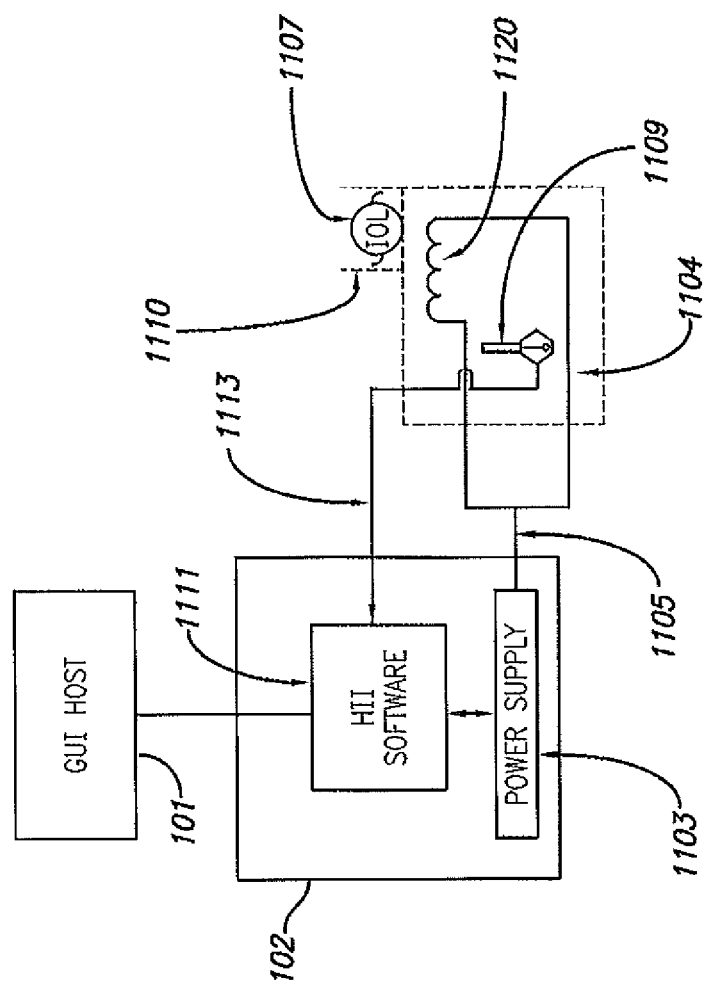
FIG. 11A illustrates a sterile heating element or container with temperature sensing that may be employed in accordance with the present design.

FIG. 11A illustrates a phacoemulsification system instrument host 102 configured to provide power for a sterile heating element, or container with an integrated heating element, with temperature sensing that may be employed in accordance with another aspect of the present design. In this configuration, the design may employ power supply 1103 to drive sterile heating element 1104 using heater 1120 in conjunction with integrated temperature sensor 1109. The surgeon or other operating room personnel may place IOL 1107 on or proximate to the sterile heating element 1104 to warm the IOL.

In a manner similar to the methods previously described, instrument host 102 may provide software control and monitoring facilities for heating using sterile heating element 1104, with heat transferred from sterile heating element 1104 into IOL 1107 prior to folding, rolling, and manipulating the IOL.

In the FIG. 11A arrangement, the surgeon, or surgical room personnel, may cause or ensure connection between power supply 1103 and sterile heating element 1104 using cable 1105 for the power distribution path. After placing IOL 1107 in contact with or proximate to sterile heating element 1104, such as by fixture 1110 holding the IOL during warming, instrument host 102 may be operated by inputting settings and selections using GUI Host 101. Such values may include but are not limited to desired temperature, desired temperature increase from existing, or some other temperature parameter establishing desired control of heat transfer from sterile heating element 1104 into IOL 1107.

Instrument host 102 may execute HII software 1111 and provide instructions for operating power supply 1103 while monitoring the measured temperature of sterile heating element 1104 measured and reported from integrated temperature sensor 1109, thus providing a feedback loop and controlling the temperature conditions to the conditions desired. In this arrangement, integrated temperature sensor 1109 may communicate measured temperature values to HII software 1111 across communication connection path 1113.

Figure 11B:
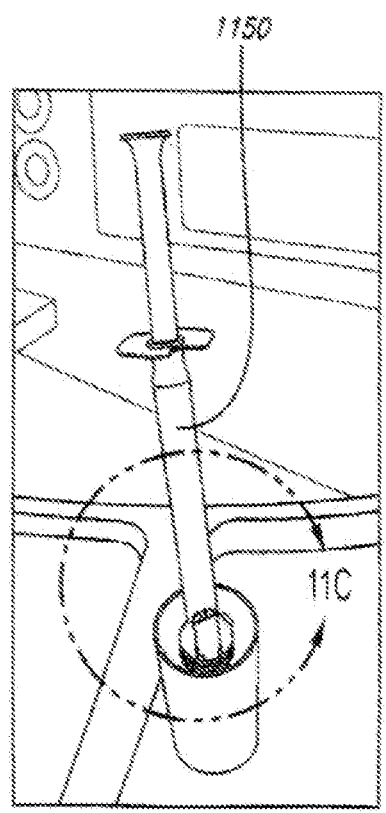
FIG. 11B illustrates a phacoemulsification insertion system injector or injection device with a heater located in the sterile field wherein heat transfer may involve either wet or dry applications.
Figure 11C:
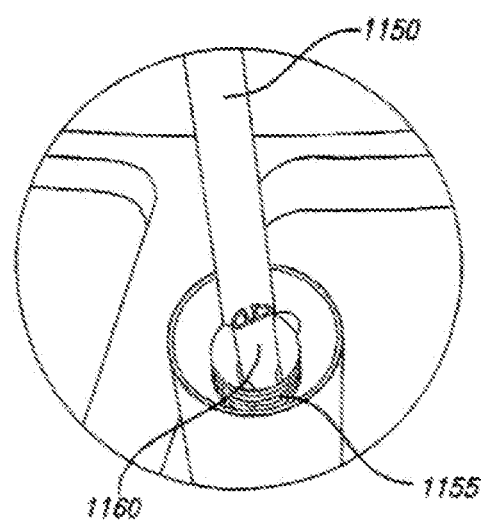
FIG. 11C is an exploded view of a portion of an embodiment of FIG. 11B.

FIG. 11B illustrates an embodiment for a phaco system injection device with a heater located in the sterile field where heat transfer into the injection device may involve either a wet or dry heat transfer mechanism. In one configuration, the present design may transfer heat from an "ink well" like heater arrangement placed in the sterile field where the phaco system may provide power for the heater. The present design's "ink well" may provide for a dry or wet method for heat transfer to injector handpiece 1150. Referring to the exploded view illustrated in FIG. 11C, heater "ink well" 1155 may be electrically connected to the instrument host and power the electric heater element, not shown, while contained within the sterile field. The surgeon may place cartridge 1160 into ink well 1155 for warming the IOL held within the cartridge. When at the desired temperature, the surgeon may move cartridge 1160 from the ink well to the patient's eye for insertion by manipulating injector handpiece 1150.

Figure 12A:
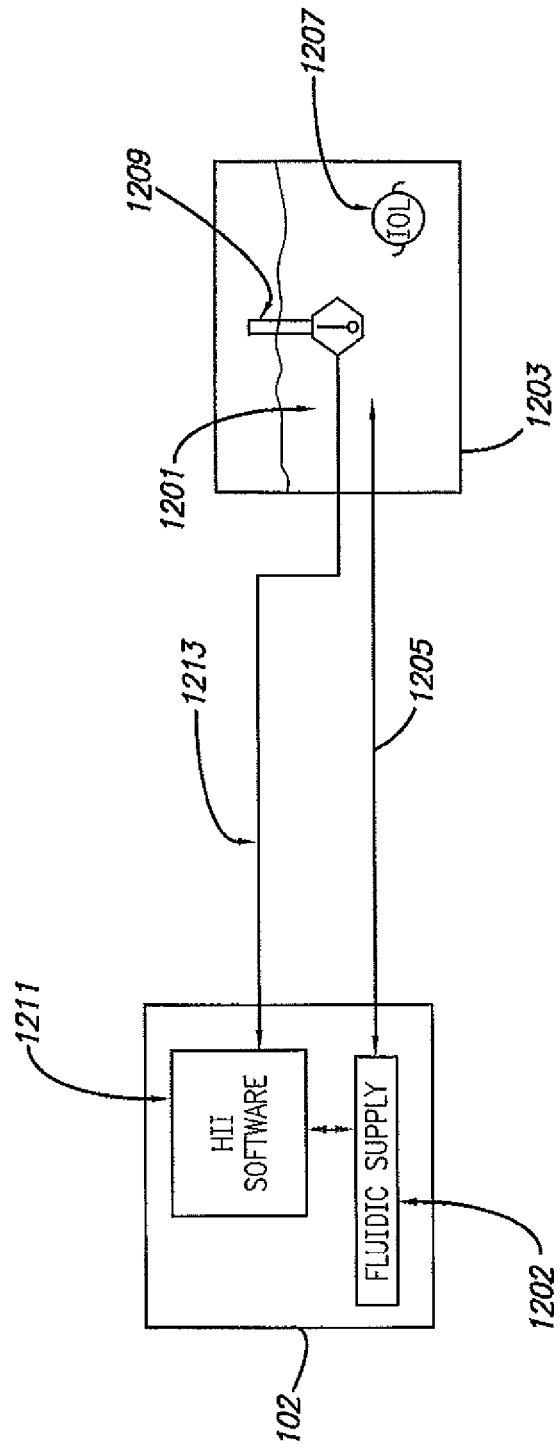
FIG. 12A is a design configured to warm fluid, such as water, and heat the IOL with temperature sensing that may be employed in accordance with the present design.

FIG. 12A illustrates an instrument host 102 having fluidic supply system 1202 configured to generate warm fluid (e.g. water or BSS) for heating the IOL with temperature sensing. In this configuration, fluidic supply 1202 may supply warm liquid solution 1201, such as water or BSS, to wet fixture 1203 with temperature sensor 1209 where IOL 1207 is contained and/or suspended by liquid solution 1201 or some other appropriate fluid. Phacoemulsification instrument host 102 controls and monitors the warming of IOL 1207, allowing the surgeon to manipulate an appropriately heated lens prior to insertion and delivery into the eye.

Surgical room personnel may ensure connection between fluidic supply 1202 and wet fixture 1203 using tubing at 1205. This arrangement cycles liquid solution 1201 through the instrument host for warming. After placing IOL 1207 in contact with liquid solution 1201, operating room personnel may input settings and selections to control heat transfer from fluidic supply 1202 into the liquid solution. Desired temperature, temperature change from present temperature, or any other appropriate value may be provided and employed by the system. HII software 1211 provides instructions to operate fluidic supply 1202 while monitoring the measured temperature of liquid solution 1201 measured and reported from temperature sensor 1209. In this arrangement, temperature sensor 1209 communicates measured temperature values to HII software 1211 across communication connection path 1213. Control and response employs this feedback loop to achieve and maintain the set temperature readings/levels.

Figure 12B:
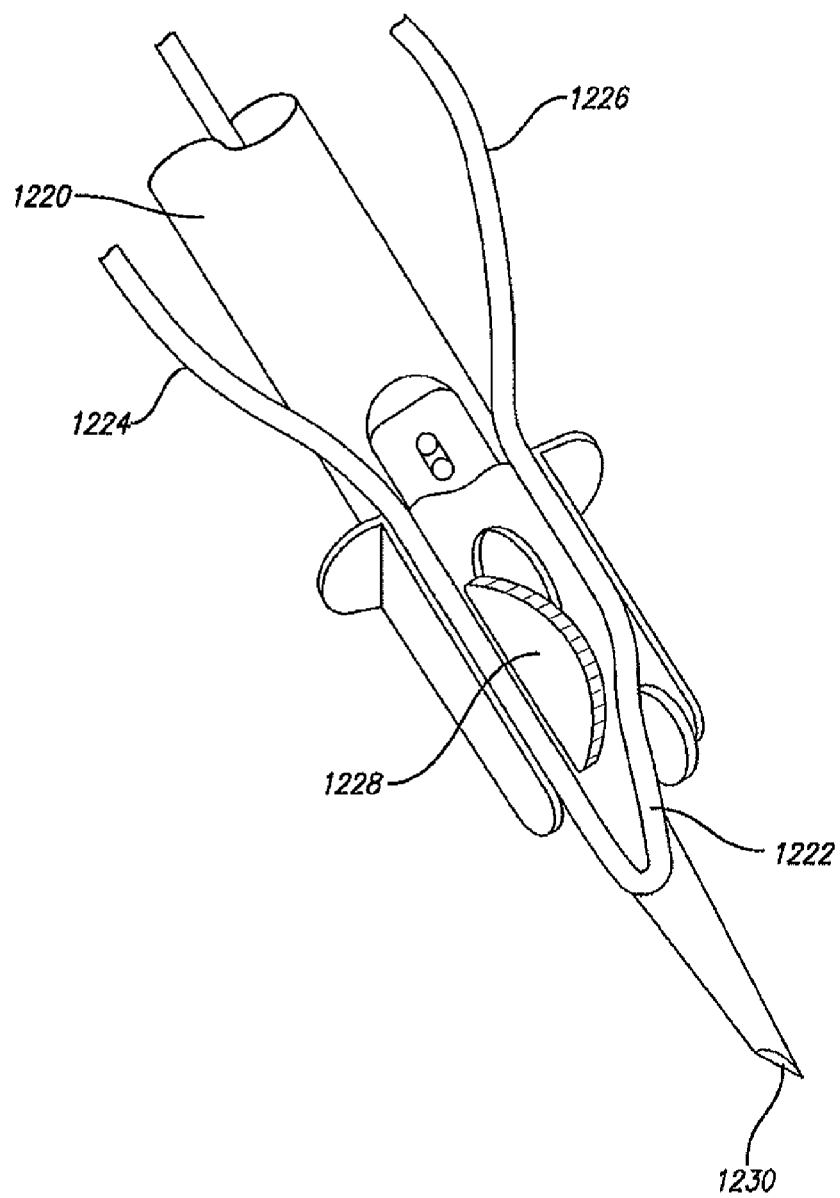
FIG. 12B illustrates a phacoemulsification insertion system injector or injection device that heats a cartridge via a water jacket with wastewater provided from the phacoemulsification system.

FIG. 12B shows an IOL insertion system "injector" that heats the IOL cartridge via a water jacket with wastewater, or other suitable fluid, provided from the phaco system. In this arrangement, handpiece 1220 may move fluid between a heat exchanger located on the phaco system and water jacket 1222. To move fluid between the heat exchanger and the water jacket, the present design may arrange for water inlet tube 1224 to supply water from the instrument host to the water jacket and for water outlet tube 1226 to return water from water jacket 1222 to the heat exchanger, not shown, within the instrument host. The phaco system may pump heated fluid through water jacket 1222, routing through water inlet tube 1224 and water outlet tube 1226, and may provide heat to warm folded IOL 1228 loaded into the cartridge. Heat is transferred into the folded IOL via water jacket ports, not shown, molded within the cartridge. When at the desired temperature, the surgeon may move IOL 1228 from the cartridge to the patient's eye through distal tip 1230 by manipulating handpiece 1220.

Figure 13:
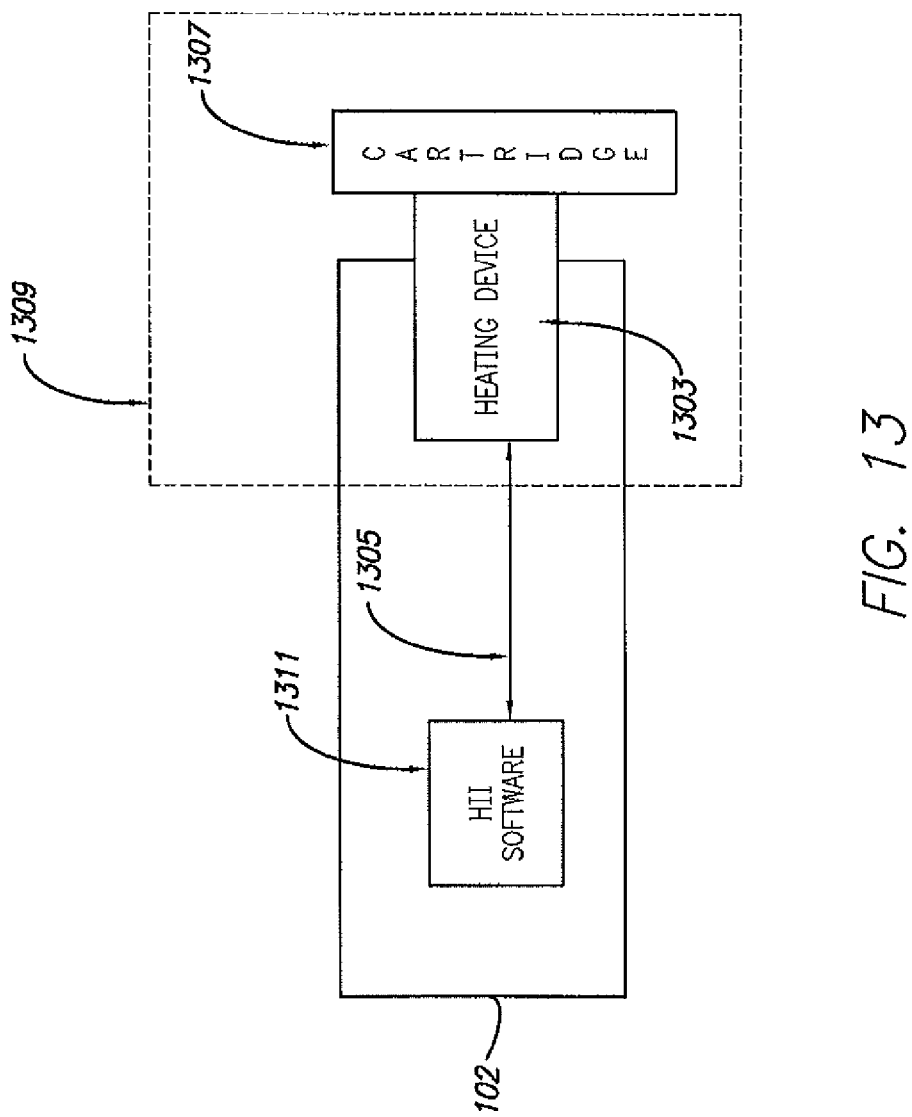
FIG. 13 illustrates a heating device configured to receive an IOL inserter cartridge with temperature sensing that may be employed with the present design.

FIG. 13 is a phacoemulsification instrument host configured to receive an IOL inserter cartridge that employs temperature sensing. In this configuration, a heating device 1303 warms insertion cartridge 1307. HII software 1311 may control the heating device 1303 via connection path 1305. Heating device 1303 may include a temperature sensor (not shown) and may communicate measured temperatures from heating device 1303 to HII software 1311 via the same or a separate connection path. The IOL is contained within cartridge 1307. Phacoemulsification instrument host 102 may control and monitor the heating of insertion cartridge 1307 using HII software 1311.

Operating room personnel may confirm connection between heating device 1303 and instrument host 102 using connection path 1305 for power distribution and temperature sensing. After placing insertion cartridge 1307 in contact with heating device 1303, for example by plugging the cartridge into an electrical connection available on heating device 1303, operating room personnel may provide settings and selections to control heat transfer from heating device 1303 into the insertion cartridge 1307. HII software 1311 provides instructions to operate heating device 1303 while monitoring the temperature of heating device 1303 using an integrated temperature sensor (not shown). The temperature sensor communicates measured temperature values to HII software 1311 across communication connection path 1305. FIG. 13 illustrates operation in a sterile field 1309, however the design may be operated outside of field 1309 if desired.

Figure 14A:
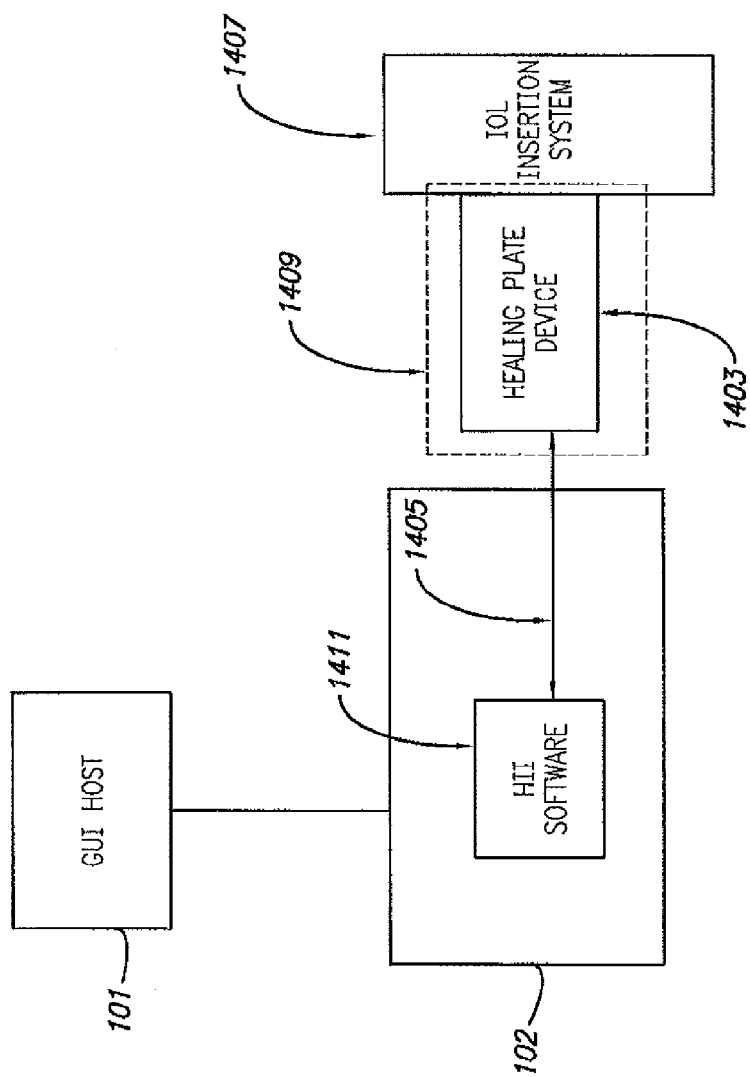
FIG. 14A is a heated plate device arranged to transfer heat to an IOL with temperature sensing that may be employed with the present design.

FIG. 14A shows a heated well, or plate, arranged to transfer heat to an IOL. Heating plate device 1403 is employed to warm IOL insertion system 1407. HII software 1411 may operate the heating plate device via connection path 1405, and heating plate device 1403 may include a temperature sensor (not shown). Measured temperatures may be provided from heating plate device 1403 to HII software 1411 via connection path 1405. In the arrangement shown, the IOL is contained within IOL insertion system 1407, but other heating arrangements may be employed.

Operating room personnel can verify a connection between heating plate device 1403 and instrument host 102 using connection path 1405 for power distribution and temperature sensing. After placing IOL insertion system 1407 in contact with heating plate device 1403, for example by plugging the IOL insertion system into a connection available on heating plate device 1403, operating room personnel may provide settings and selections to control heat transfer from heating plate device 1403 to the IOL insertion system 1407. HII software 1411 may provide instructions to operate heating plate device 1403 while monitoring the measured temperature of the device measured and reported from the integrated temperature sensor, not shown. In this arrangement, the temperature sensor may communicate measured temperature values to HII software 1411 across communication connection path 1405. HII software 1411 provides for temperature sensing and control using a feedback control loop.

In this arrangement the heating plate device 1403 and IOL insertion system 1407 may be contained in a sterile field, where the heating plate device, or a heating well, may be placed under sterile drape 1409, but this arrangement may operate without sterile drape 1409. In addition, an inferred light source may be substituted for heating plate device 1403 where the inferred light source may be positioned above or on a dedicated stand that may be placed over the sterile field and directed towards a loaded injector positioned on a tray. The instrument host may provide power to operate the inferred light source.

Figure 14B:
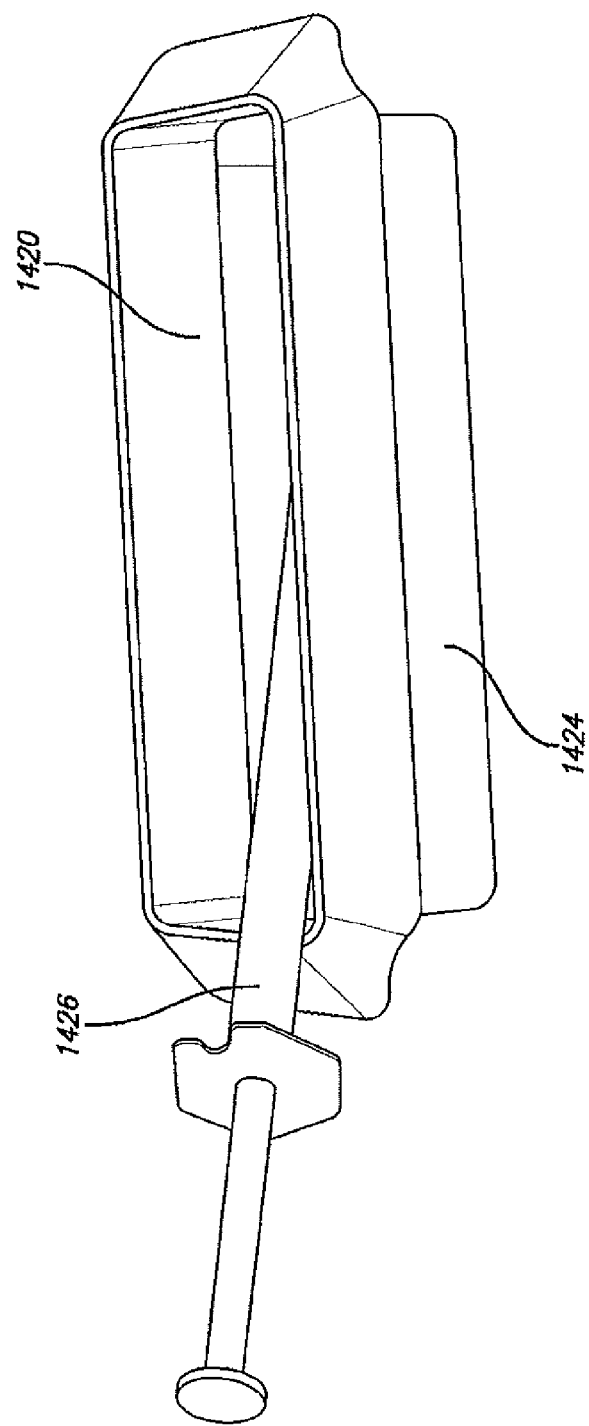
FIG. 14B illustrates a well located in a sterile field where irrigation fluid is used in the well to warm the injector.

FIG. 14B illustrates a 'well' or 'tank' 1420 located in a sterile field where irrigation fluid is used in the well to warm the injector. Well 1420 may be positioned within a sterile field at 1424 in an arrangement suitable for transferring heat into loaded injector handpiece 1426. In this embodiment, the present design's well 1420 may receive irrigation fluid from the phaco system to conduct heat into injector handpiece 1426, thereby warming the IOL prior to use.

In an alternate embodiment, the present design may be configured for heating an ophthalmic viscosurgical device (OVD). The warmed OVD may be used by the surgeon as a lubricant and a heat source for the IOL insertion system previously disclosed.

Figure 15:
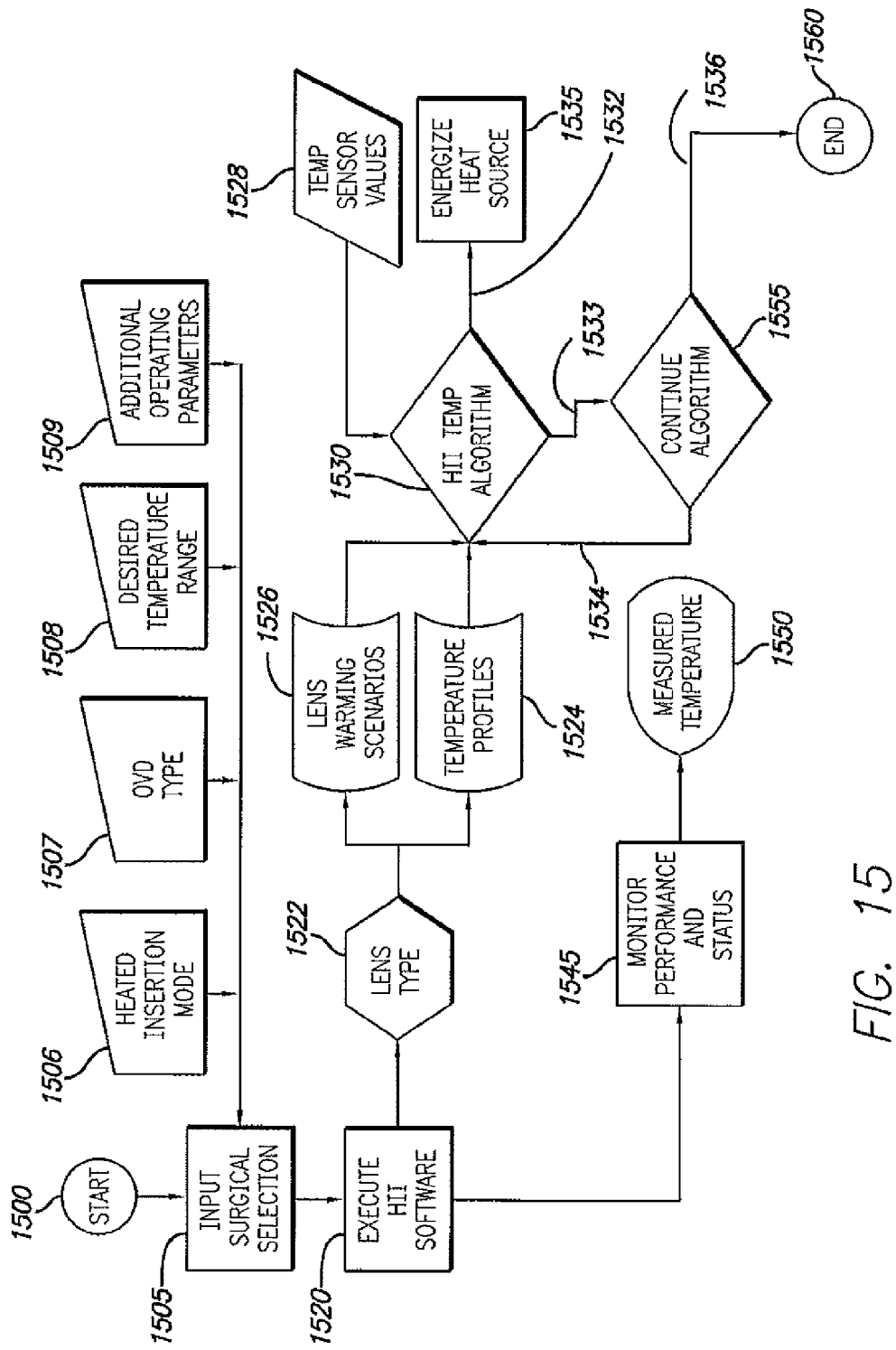
FIG. 15 is a flowchart illustrating general operation of the HII (heated IOL insertion) system to control heated delivery and warm an IOL prior to use.

FIG. 15 is a flowchart illustrating general operation of the system software to control heated delivery for warming an IOL prior to implantation in accordance with an aspect of the present design. The surgeon may operate the HII software to control the warming of an IOL, IOL cartridge, or IOL insertion system by operating the instrument host to start software operation at point 1500. The surgeon or other operating room personnel may input surgical selections at point 1505, establishing desired operating parameters and settings, including for example selecting heated insertion mode 1506, selecting OVD type 1507, temperature range 1508, and additional operating parameters 1509. Additional operating parameters 1509 may include but are not limited to type of IOL design, and/or IOL cartridge size. Input for desired temperature range 1508 may further establish or include the desired liquid solution and lens temperature measured within the wet fixture.

In one arrangement, executing HII software 1520 algorithms and processes may use preset values, for example once the surgeon selects lens type 1522, the present design may load a previously stored temperature profile 1524 and lens warming scenario 1526, i.e. time parameters, with default values stored locally. The surgeon may choose, using surgical selections 1505, to use or modify these default values prior to and during the ocular implant procedure.

During operation, instrument host 102 may receive measured temperature sensor values 1528, or signals relating temperature values, and may calculate desired or desirable heating levels using selected desired temperature range 1508 with reported temperature sensor values 1528. HII software may determine whether the measured values reported by the temperature sensor are within or out of the desired settings. In the situation where the reported temperature is below the desired temperature, HII algorithm 1530 may determine to start heating the IOL by signaling at 1532 to energize heat source 1535. In the situation where the desired IOL temperature has been reached, HII algorithm 1530 may determine to stop providing heat transferred into the IOL removing the signal at 1532, thus de-energizing heat source 1535.

Algorithm 1530 may provide signal at point 1533 to continue algorithm 1555 instructing the software to continue operation by signaling at 1534 to keep HII algorithm 1530 alive, or signaling at 1536 to stop or end software operation at point 1560. Continue algorithm 1555 may provide for automated comparison between the desired and measured solution temperature, received from the temperature sensor, and may store selected temperature values or settings.

The HII software's HII temperature algorithm 1530 may continue at point 1534 to monitor and compare reported temperature with the desired range to ensure proper heating of the IOL, IOL cartridge, or IOL insertion system during the procedure. HII software may allow the surgeon to observe an increase in IOL temperature while energizing the heat source and may readily compare currently observed temperature to their desired settings.

The system may provide an alarm to the surgeon in a situation where liquid solution temperature is too high and may instruct the surgeon, for example, to remove power from the ultrasonic needle, refer to the embodiment illustrated in FIG. 8, and remove the rod from the liquid solution containing the IOL.

Executing HII software 1520 may allow the surgeon to monitor HII system performance and status 1545, including but not limited to receiving and processing signals relating measured operating values received from sensors, or instrument host 102 arranged in the present design for near real-time rendering measured temperature 1550 and other values, displayed at GUI host 101, such as the actual system operating characteristics such as ambient temperature and humidity and lens temperature.

While it is noted that the embodiments herein describe heating of IOLs, it is to be understood that cooling of the articles may occur using the present design. For example, rather than a warm fluid, a cold fluid may be provided and the IOLs cooled. Such a design may be beneficial in warm environments or for components that are sterilized prior to insertion using heat in excess of room or body temperature. A cool fluid well may be provided, for example, in accordance with one of the embodiments disclosed herein.

Systems illustrated in FIG. 1 through 15 simply show components and devices that may be used within the present design. The size and shape of the components illustrated are not to scale nor accurately sized, and note that certain components, notably ultrasonic handpiece 110, may interface with the liquid solution but in actuality instrument host 102 provides for powering the attached handpiece device. Further, more or fewer components may be included in the system than are shown in the figures depending on the circumstances and implementation of the heat generating source and transfer mechanism configuration.

The present design, including the software and functionality disclosed herein, may be implemented in a phacoemulsification/vitrectomy device or in or in association with any type of computing device, including but not limited to a personal computer, processor, or other hardware, firmware, or software configured to perform the functionality discussed herein.

In sum, the present design may provide for the establishing and maintaining of a desired IOL temperature, and may dynamically adjust to vary the operation of the heat source based on environmental conditions. The present design may involve a wide range of heat generation and transfer methods for the warming of an IOL prior to use. For example, the heat source may be cycled on and off over time to maintain a desired IOL temperature, where the heat source duty rate may be increase for cooler operating room environments, and the duty rate may be decreased for warmer environments, in accordance with the desired/selected parameters input by the surgeon.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for providing an intra-ocular lens (IOL) to an eye through an incision in the eye, comprising: assessing IOL insertion conditions; translating said IOL insertion conditions into a desired force range for insertion of the IOL via the incision; controlling a power source delivery device to apply force to the IOL generally within the desired force range to move the IOL to the eye; and monitoring conditions while controlling the power source delivery device, said conditions comprising force encountered in moving the IOL into the eye pursuant to said controlling; wherein said controlling employs feedback of the force encountered and selectively alters force applied based on force encountered.

2. The method of claim 1, wherein said controlling causes force to be applied to a rod configured to direct said IOL through the incision into the eye.

3. The method of claim 2, wherein said controlling comprises applying forces to the rod, said forces comprising at least one selected from a group consisting of linear force, rotational force, and vibrational force.

4. The method of claim 1, wherein the IOL is provided to the eye while substantially at a desired temperature.

5. The method of claim 1, wherein the power source delivery device comprises at least one selected from a group consisting of: a device configured to provide hydraulic pressure; a device configured to provide pneumatic pressure; and a device configured to provide mechanical pressure based on electrical signals.

6. The method of claim 1, wherein IOL insertion conditions comprise at least one selected from a group consisting of: lens temperature; lens environment temperature; ambient humidity; ambient pressure; lens diopter; IOL design; cartridge size when force is applied to the IOL while within a cartridge; and force limits.

7. The method of claim 1, wherein said controlling a power source delivery device comprises engaging the power source delivery device to move the IOL into the eye through the incision using force.

8. The method of claim 1, further comprising enabling a user to establish desired IOL application parameters, and wherein said IOL application parameters are employed in said controlling.

9. An apparatus configured to provide an intra-ocular lens (IOL) to an eye through an incision in the eye, comprising: a processing device configured to assess IOL insertion conditions and translate said IOL insertion conditions into a desired force range for insertion of the IOL via the incision; and a power source delivery device configured to apply force to the IOL generally within the desired force range to move the IOL to the eye; wherein the processing device is configured to monitor conditions while controlling the power source delivery device, said conditions comprising force encountered in moving the IOL into the eye, and wherein said processing device employs feedback of the force encountered and selectively alters force applied based on force encountered.

10. The apparatus of claim 9, wherein the power source delivery device causes force to be applied to a rod configured to direct said IOL through the incision into the eye.

11. The apparatus of claim 9, wherein the power source delivery device causes the IOL to be provided to the eye while the IOL is substantially at a desired temperature.

12. The apparatus of claim 9, wherein the power source delivery device is controlled by the processing device to apply forces to the rod, said forces comprising at least one selected from a group consisting of linear force, rotational force, and vibrational force.

13. The apparatus of claim 9, wherein the power source delivery device comprises at least one selected from a group consisting of: a device configured to provide hydraulic pressure; a device configured to provide pneumatic pressure; and a device configured to provide mechanical pressure based on electrical signals.

14. The apparatus of claim 9, wherein IOL insertion conditions comprise at least one selected from a group consisting of: lens temperature; lens environment temperature; ambient humidity; ambient pressure; lens diopter; IOL design; cartridge size when force is applied to the IOL while within a cartridge; and force limits.

15. The apparatus of claim 9, wherein said controlling a power source delivery device comprises engaging the power source delivery device to move the IOL into the eye through the incision using force.

16. A phacoemulsification apparatus, comprising: a processor configured to assess IOL insertion conditions and translate said IOL insertion conditions into a desired force range for insertion of an IOL into an eye; and a power source configured to cause force to be applied to the IOL, the force generally within the desired force range, the force sufficient to move the IOL toward the eye; wherein the processor is configured to monitor conditions while controlling the power source, said conditions comprising force encountered in moving the IOL into the eye, and wherein said processing device employs feedback of the force encountered and selectively alters force applied based on force encountered.

17. The apparatus of claim 16, wherein the power source causes force to be applied to a rod configured to direct said IOL through an incision into the eye.

18. The apparatus of claim 16, wherein the power source causes the IOL to be provided to the eye while the IOL is substantially at a desired temperature.

19. The apparatus of claim 16, wherein the power source is controlled by the processor to apply forces to the rod, said forces comprising at least one selected from a group consisting of linear force, rotational force, and vibrational force.

20. The apparatus of claim 16, wherein the power source comprises at least one selected from a group consisting of: a device configured to provide hydraulic pressure; a device configured to provide pneumatic pressure; and a device configured to provide mechanical pressure based on electrical signals.

21. The apparatus of claim 16, wherein IOL insertion conditions comprise at least one selected from a group consisting of: lens temperature; lens environment temperature; ambient humidity; ambient pressure; lens diopter; IOL design; cartridge size when pressure is applied to the IOL while within a cartridge; and force limits.

22. The apparatus of claim 16, wherein the power source causes the IOL to move toward the eye using force.

* * * * *